(12) United States Patent
Hunt

(10) Patent No.: US 12,121,316 B2
(45) Date of Patent: *Oct. 22, 2024

(54) ARTICULATED TOOL POSITIONER FOR ROBOTIC SURGERY SYSTEM

(71) Applicant: Titan Medical Inc., Toronto (CA)

(72) Inventor: Timothy Brandon Hunt, Hollywood, FL (US)

(73) Assignee: Titan Medical Inc., Toronto (CA)

( * ) Notice: Subject to any disclaimer, the term of this patent is extended or adjusted under 35 U.S.C. 154(b) by 217 days.

This patent is subject to a terminal disclaimer.

(21) Appl. No.: 17/513,933

(22) Filed: Oct. 29, 2021

(65) Prior Publication Data

US 2022/0047349 A1 Feb. 17, 2022

Related U.S. Application Data

(63) Continuation of application No. 16/235,071, filed on Dec. 28, 2018, now Pat. No. 11,234,783.

(51) Int. Cl.
*A61B 34/00* (2016.01)
*A61B 34/30* (2016.01)
(Continued)

(52) U.S. Cl.
CPC .............. *A61B 34/71* (2016.02); *A61B 34/30* (2016.02); *A61B 90/11* (2016.02);
(Continued)

(58) Field of Classification Search
CPC ................... A61B 34/71; A61B 34/30; A61B 2017/00477; A61B 2034/301; A61B 2034/302; A61B 2034/306

See application file for complete search history.

(56) References Cited

U.S. PATENT DOCUMENTS

| 5,448,989 A | 9/1995 | Heckele |
| 5,716,354 A | 2/1998 | Hluchy |

(Continued)

FOREIGN PATENT DOCUMENTS

| JP | 2008220971 A | 9/2008 |
| WO | 2006057702 A2 | 6/2006 |

(Continued)

OTHER PUBLICATIONS

Decision to Grant European patent received in European Application No. 13887243.7, dated May 11, 2017.

(Continued)

*Primary Examiner* — Sarah A Long
(74) *Attorney, Agent, or Firm* — Carter, DeLuca & Farrell LLP

(57) ABSTRACT

In some embodiments, an insertion device for a robotic surgery apparatus can include one or more guides configured to receive and/or engage a plurality of control links. The one or more guides can each include a plurality of channels. The insertion device can include a tool interface configured to engage one or more surgical tools for performing a surgical procedure. At least one control link of the first, second, or third pluralities of control links can be overlapping, coaxially aligned, or otherwise placed in a nested configuration with respect to another control link of the first, second, or third pluralities of control links. One or more of the plurality of first, second, or third control links can be configured to be actuated to adjust spatial position of the tool interface to facilitate repositioning of the surgical tool.

21 Claims, 13 Drawing Sheets

(51) Int. Cl.
*A61B 90/11* (2016.01)
*A61B 17/00* (2006.01)

(52) U.S. Cl.
CPC .............. *A61B 2017/00477* (2013.01); *A61B 2034/301* (2016.02); *A61B 2034/302* (2016.02); *A61B 2034/306* (2016.02)

(56) References Cited

U.S. PATENT DOCUMENTS

| | | | |
|---|---|---|---|
| 7,147,650 | B2 | 12/2006 | Lee |
| 7,320,700 | B2 * | 1/2008 | Cooper ................. A61B 17/29 600/101 |
| 7,364,582 | B2 | 4/2008 | Lee |
| 7,367,973 | B2 | 5/2008 | Manzo et al. |
| 7,591,783 | B2 * | 9/2009 | Boulais ................ A61B 1/0008 600/141 |
| 7,682,307 | B2 | 3/2010 | Danitz et al. |
| 8,182,417 | B2 * | 5/2012 | Danitz ................. A61B 1/0055 606/1 |
| 8,347,754 | B1 | 1/2013 | Veltri et al. |
| 9,033,998 | B1 | 5/2015 | Schaible |
| 9,629,688 | B2 | 4/2017 | Robert et al. |
| 11,234,783 | B2 | 2/2022 | Hunt |
| 2003/0045778 | A1 | 3/2003 | Ohline et al. |
| 2003/0135204 | A1 | 7/2003 | Lee et al. |
| 2004/0199052 | A1 | 10/2004 | Banik et al. |
| 2005/0059960 | A1 | 3/2005 | Simaan et al. |
| 2005/0096502 | A1 | 5/2005 | Khalili |
| 2005/0096694 | A1 | 5/2005 | Lee |
| 2005/0251112 | A1 | 11/2005 | Danitz et al. |
| 2005/0273085 | A1 | 12/2005 | Hinman et al. |
| 2006/0199999 | A1 | 9/2006 | Ikeda et al. |
| 2007/0135803 | A1 | 6/2007 | Belson |
| 2008/0045803 | A1 | 2/2008 | Williams et al. |
| 2008/0064921 | A1 | 3/2008 | Larkin |
| 2008/0287963 | A1 | 11/2008 | Rogers |
| 2009/0171374 | A1 | 7/2009 | Omori |
| 2009/0299344 | A1 | 12/2009 | Lee et al. |
| 2010/0004509 | A1 | 1/2010 | Naito et al. |
| 2010/0262161 | A1 | 10/2010 | Danitz et al. |
| 2011/0295242 | A1 | 12/2011 | Spivey et al. |
| 2012/0232339 | A1 | 9/2012 | Csiky |
| 2012/0253131 | A1 | 10/2012 | Malkowski et al. |
| 2012/0253325 | A1 | 10/2012 | Sniffin et al. |
| 2013/0023923 | A1 | 1/2013 | Mueller |
| 2013/0090763 | A1 | 4/2013 | Simaan et al. |
| 2013/0123783 | A1 | 5/2013 | Marczyk et al. |
| 2014/0046305 | A1 | 2/2014 | Castro |
| 2015/0202013 | A1 | 7/2015 | Teichtmann |
| 2016/0143633 | A1 | 5/2016 | Robert et al. |
| 2018/0028779 | A1 | 2/2018 | von Oepen et al. |

FOREIGN PATENT DOCUMENTS

| | | |
|---|---|---|
| WO | 2010098871 A2 | 9/2010 |
| WO | 2012078309 A2 | 6/2012 |
| WO | 2012138834 A2 | 10/2012 |
| WO | 2013082310 A1 | 6/2013 |
| WO | 2014201538 A1 | 12/2014 |

OTHER PUBLICATIONS

Examiner Requisition re5b4ceived in Canadian Application No. 2,913,943, dated Jan. 16, 2017.
Examiner Requisition received in Canadian Application No. 2,913,943, dated Jun. 6, 2017.
Examiner Requisition received in Canadian Application No. 2,913,943, dated Dec. 29, 2017.
Extended European Search Report and Written Opinion received in European Application No. 17171068.4, dated Sep. 28, 2017.
International Search Report mailed by Canadian Intellectual Property Office dated Mar. 5, 2014 in PCT Application No. PCT/CA2013/001076 in 5 pages.
Notice of Allowance received in Canadian Application No. 2,913,943, dated Apr. 24, 2018.
The extended European search report issued by European Patent Office dated May 23, 2016 in the corresponding European Patent Application No. 13887243.7—9 pages.
Written Opinion received in PCT Application No. PCT/CA2013/001076, dated Feb. 19, 2014 in 6 pages.

* cited by examiner

ARTICULATED TOOL POSITIONER FOR ROBOTIC SURGERY SYSTEM

CROSS-REFERENCE TO RELATED APPLICATION

The present application is a Continuation Application claiming the benefit of and priority to U.S. patent application Ser. No. 16/235,071, filed on Dec. 28, 2018, the entire content of which is incorporated herein by reference.

TECHNICAL FIELD

This disclosure relates generally to robotic surgical manipulators and articulated tool positioners for performing a medical procedure.

DESCRIPTION OF RELATED ART

Articulated tool positioning devices are used to perform medical and surgical procedures, such as laparoscopic surgery and computer assisted robotic surgery, within a body cavity of a patient. An articulated tool positioner generally includes a device to control insertion of a visualization devices and/or one or more instruments during the surgical procedure. Known articulating tool positioning systems suffer from a variety of shortcomings, including large size, poor resolution of curvature, lack of reliability, and the like. The present disclosure overcomes these and other problems associated with known articulated tool positioning systems, methods, and apparatuses.

SUMMARY

In some cases, an insertion device for a robotic surgery apparatus can include one or more guides each comprising a plurality of channels. The insertion device can include a tool or instrument interface configured to engage a surgical tool or instrument configured to perform robotic surgery. The insertion device can include one or more pluralities of control links configured to be actuated to cause the one or more guides to assume positions that selectively define a substantially continuous curve.

The insertion device can include a first plurality of control links can each comprise a first end portion configured to engage a second guide. One or more of the first plurality of control links can extend through a respective channel of a first guide.

The insertion device can include a second plurality of control links can each comprise a first end portion configured to engage the first guide and a second end portion configured to engage a third guide. One or more of the second plurality of control links can extend through a respective channel of the second guide.

The insertion device can include a third plurality of control links can each comprise a first end portion configured to engage the tool interface. One or more of the third plurality of control links can extend through respective channels of the third guide and can further extend through the respective channels of the second guide. One or more (e.g., each of) of the third plurality of control links can include a portion that passes through and/or is coaxially aligned with a respective second control link of the second plurality of control links.

One or more of the second plurality of control links can be configured to cause the third guide to maintain an orientation generally the same as the first guide when any of the first plurality of control links and third plurality of control links is actuated.

One or more of the third plurality of control links can be configured to be actuated to cause the tool interface to be selectively moved into any of a plurality of orientations defining a substantially continuous curve from the third guide to the tool interface.

One or more of the first, second, and/or third pluralities of control links can be configured to be actuated to adjust spatial position of the tool interface to facilitate repositioning of the surgical tool.

The insertion device of any of preceding paragraphs and/or any of insertion devices described below can include one or more of the following features. The insertion device can further comprise a support cover configured to inhibit at least one of: displacement of one or more of the first plurality of control links from the respective channel of the first guide, displacement of one or more of the second plurality of control links from the respective channel of the second guide, or displacement of one or more of the third plurality of control links from the respective channel of the second guide. The support cover can include an external sheath, a coil, or both such that the external sheath covers the coil. One or more of the channels of the first guide, second guide, and/or third guide can be sized to receive a respective control link of any one of the first plurality of control links, the second plurality of control links, or the third plurality of control links. One or more of the first, second, and/or third pluralities of control links can include a hollow interior portion through which the portion of another one the first, second, and/or third pluralities of control links can pass. One or more of the first, second, and/or third pluralities of control links can include an external control link defining an internal pathway and an internal control link, such that at least a portion of the internal control link can pass through the internal pathway. The internal control link can be configured to be pulled to cause the tool interface to change position and/or to compress the external control link. The internal control link can be pulled by one or more actuators. The external control link can be configured to be compressed (e.g., pushed) to cause the tool interface to change position and/or to pull the internal control link. The external control link can be compressed by one or more actuators. The insertion device can include one or more intermediate guides. The one or more intermediate guides can be positioned between and/or engaged with at least one of the first guide, the second guide, the third guide, the tool interface, and another intermediate guide. One or more of any one of the first, second, and/or third pluralities of control links can disposed in a parallel spaced apart relation through the respective channel of at least one of the first guide, the second guide, the third guide, and the tool interface.

In some cases, a method of operating a robotic surgery apparatus includes controlling at least one surgical instrument using an insertion device of any of preceding paragraphs and/or described below.

Any of the insertion devices and/or methods of any of preceding paragraphs and/or described below can be used with any of insertion devices, methods, and/or robotic surgery systems described herein.

BRIEF DESCRIPTION OF THE DRAWINGS

Embodiments of the present disclosure will now be described hereinafter, by way of example only, with reference to the accompanying drawings in which.

DETAILED DESCRIPTION

Overview

When performing medical procedures (for example, with assistance of surgery using a robotic surgical system) one or more instruments can be inserted into a body cavity of a patient. The insertion process has some risk since instruments may inadvertently damage organs or tissue while being inserted. Incorrect positioning of the one or more instruments in the body cavity may also result in a limited range of motion within the body cavity.

As an example, when performing general surgery in the abdominal region, at least one incision would be made in a body wall of the patient's abdomen. A trocar or other access port, may then be inserted through the incision. An insertion device can be inserted through the access port and used by a surgeon to position and/or actuate one or more instruments to perform various task of a surgical site. Increased reliability when positioning the one or more instruments within the surgical site facilitate insertion of the one or more instruments and their manipulation of the surgical site.

Figure 1A:
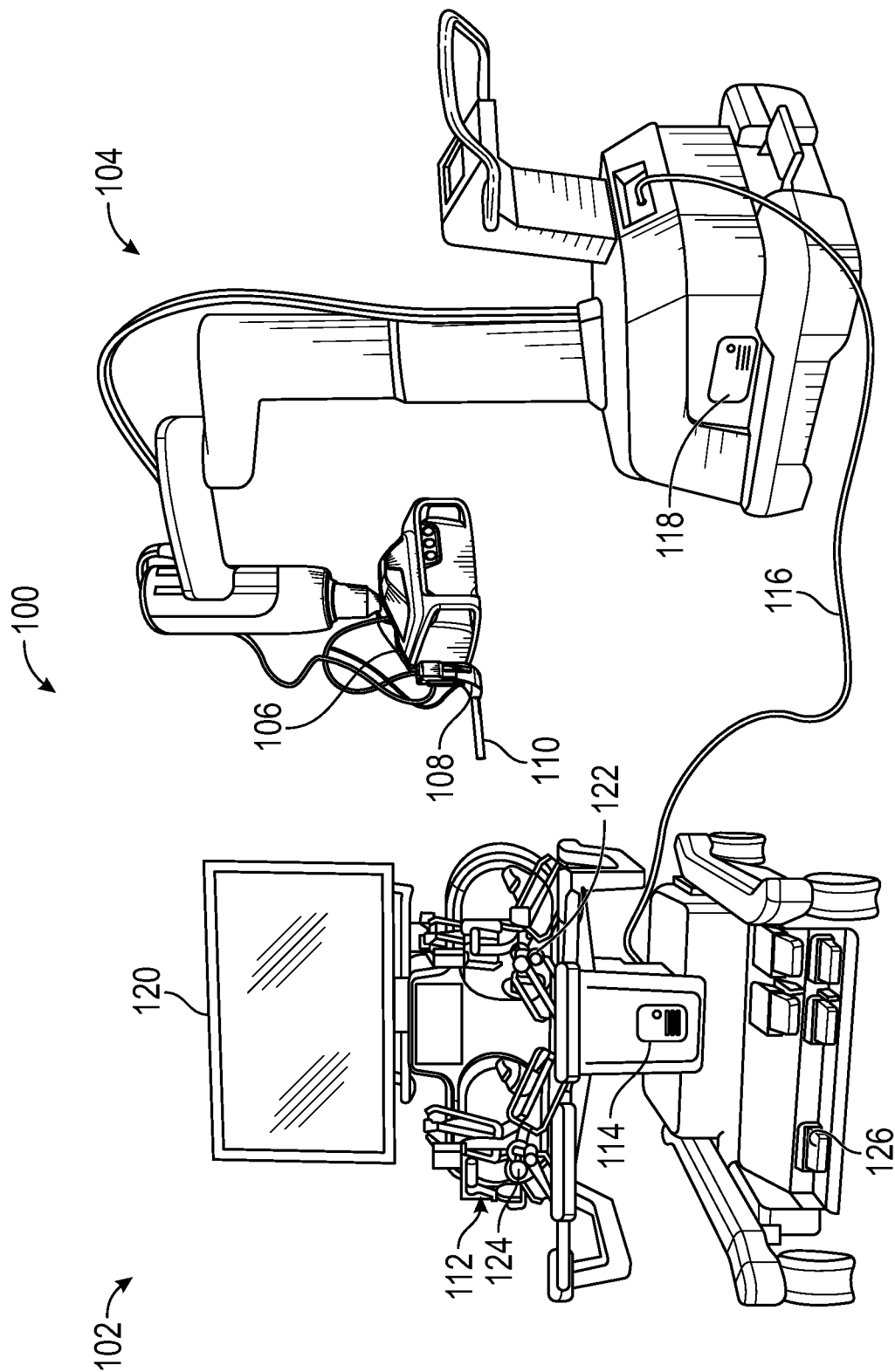
FIGS. 1A-1B illustrate a robotic surgery system in accordance with some embodiments.

Referring to FIG. 1A, a robotic surgery system in accordance with some embodiments is shown generally at 100. In some implementations, the robotic surgery system 100 can be configured to facilitate a medical procedure performed via a single incision. A single access port can be inserted into the incision to provide access for one or more instruments and cameras.

The system 100 can include a workstation 102 and a patient cart 104. The patient cart 104 can include a central unit or drive unit 106 to which instrument insertion and visualization devices 108 can be attached or mounted. The workstation 102 can include an input device 112 that receives operator (such as, a surgeon) input and produces input signals and may also be configured to generate feedback to the operator. The feedback can be visual, auditory, haptic, or the like. The input device 112 can be implemented using a haptic interface available from Force Dimension, of Switzerland, for example.

The workstation 102 can further include a master processor circuit 114 in communication with the input device 112 for receiving the input signals and generating control signals for controlling the robotic surgery system, which can be transmitted to/from the patient cart 104 via an interface cable 116. In some cases, transmission can be wireless and interface cable 116 may not be present. The input device 112 can include right and left hand controllers 122 and 124, which are configured to be grasped by the operator's hands and moved to produce input signals at the input device 112. The patient cart 104 can include a slave processor circuit 118 that receives and the control signals from the master processor circuit 114 and produces slave control signals operable to control the instrument insertion and visualization devices 108 and one or more instruments (and their respective end effectors) during a surgical procedure. The one or more instruments can include dexterous tools, such as grippers, needle drivers, staplers, dissectors, cutters, hooks, graspers, scissors, coagulators, irrigators, suction devices, that are used for performing a surgical procedure. While both master and slave processor circuits are illustrated, in other embodiments a single processor circuit may be used to perform both master and slave functions. The workstation 102 can also include a user interface, such as a display 120 in communication with the master processor circuit 114 for displaying information (such as, body cavity images) for a region or site of interest (for example, a surgical site, a body cavity, or the like) and other information to an operator. The workstation 102 can also include one or more controllers, such as one or more pedals 126, for controlling the robotic surgery system. For example, one or more pedals 126 can include a clutch pedal that allows repositioning one or more controllers 122 or 124 without corresponding movement of the associated instrument.

Figure 1B:
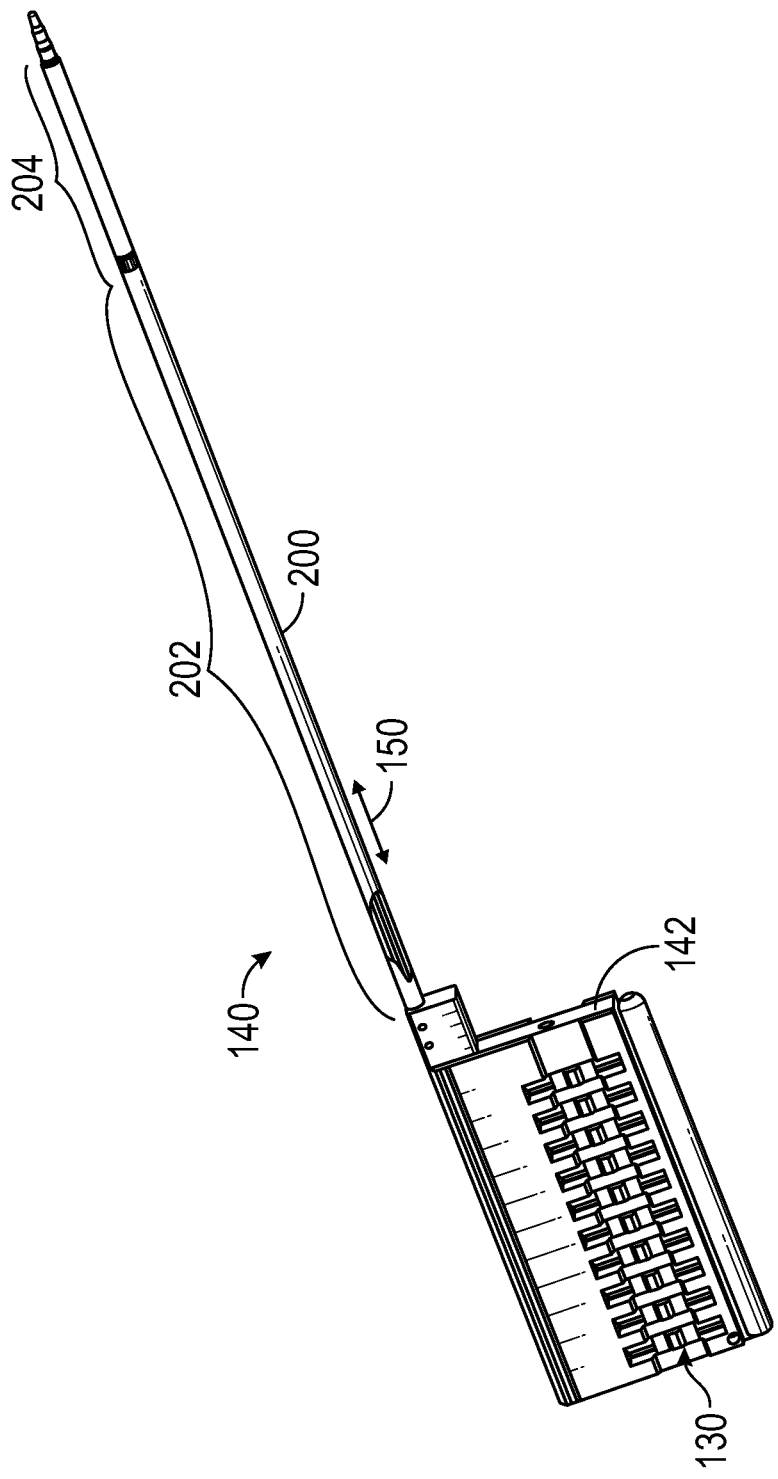

Referring to FIG. 1B, a surgical tool apparatus 140 can include an actuator housing 142 and an insertion channel configured to receive one or more elongate insertion devices 200 extending outwardly from the actuator housing 142, as described in further detail herein. The insertion device 200 includes a plurality of control links, shown in the partial cut-away on the insertion device 200. The plurality of control links (or connection or connectors) can extend along a length of the insertion device 200 and are operable to cause movement of an articulation section 204 of the insertion device 200 in response to movement of the plurality of control links in an actuating direction. The actuating direction is generally aligned with the length of the insertion device 200 and is indicated by the arrow 150.

In the embodiment shown, the insertion device 200 includes a housing 202 and an articulation section 204 including a plurality guides, as described herein. The plurality of guides are operable to move with respect to each other in response to pushing and/or pulling of the plurality of control links causing one or more portions of the articulation section 204 to assume various positions and orientations.

The surgical tool apparatus 140 can include a plurality of actuators 130. In this embodiment, the plurality of actuators 130 for positioning the articulation section 204 of the insertion device 200. In this embodiment, each of the actuators 130 is associated with a respective control link of the plurality of control links and is mounted in the actuator housing 142 to facilitate a range of travel in a transverse direction. The transverse direction is substantially orthogonal to the actuating direction 150. In the embodiment shown, each actuator 130 is received on one of a plurality of adjacently located parallel rails configured to guide the respective actuators 130 for movement in the transverse direction. The plurality of actuators 130 may include further actuators for controlling functions of the tool interface and/or a surgical tool, as described herein.

Each of the actuators 130, by travel along the transverse direction, are operable to transmit compression and/or tension forces to a respective control link to actuate the control link and respective guides. In the some instances, the plurality of actuators 130 and the associated plurality of control links are configured to place the control links of the insertion device 200 in a relaxed condition when the actuators 130 are disposed at a location within the actuator housing 142 that is offset from a center of the range of travel of the actuator by a distance.

The surgical tool apparatus can be attached to the drive unit 106, such as to the bottom of the drive unit. The drive unit 106 can include an interface that mates with the plurality of actuators 130 and controls the plurality of actuators 130 in response to one or more commands or signals from the workstation 102.

Additional details of controlling one or more of the actuators are similar to those described in U.S. Pat. No. 9,629,688, which are assigned to the assignee of the present application and the disclosure of which is incorporated by reference in its entirety.

Referring to FIGS. 2-5, in some cases, insertion devices 200 can include a housing 202 and an articulation section 204. The articulation section 204 can be located in a distal direction from the housing 202 to facilitate insertion of the articulation section 204 through an incision. The insertion device 200 can include a plurality of guides for guiding and/or engaging one or more control links within at least a portion of the articulation section 204. For example, the insertion device 200 can include a first guide 210, a second guide 230, and a third guide 250.

The insertion device 200 can include a tool interface 270 to which one or more instruments of the system 100 can be removably (or non-removably) attached. The tool interface 270 can include an opening in which the one or more instruments, such as tools used for performing a surgical procedure, can be positioned.

The insertion device 200, in various instances, can include one or more intermediate guides. For example, one or more intermediate guides can be positioned between the first guide 210 and the second guide 230; positioned between the second guide 230 and the third guide 250; and/or positioned between the third guide 250 and the tool interface 270.

Figure 5:
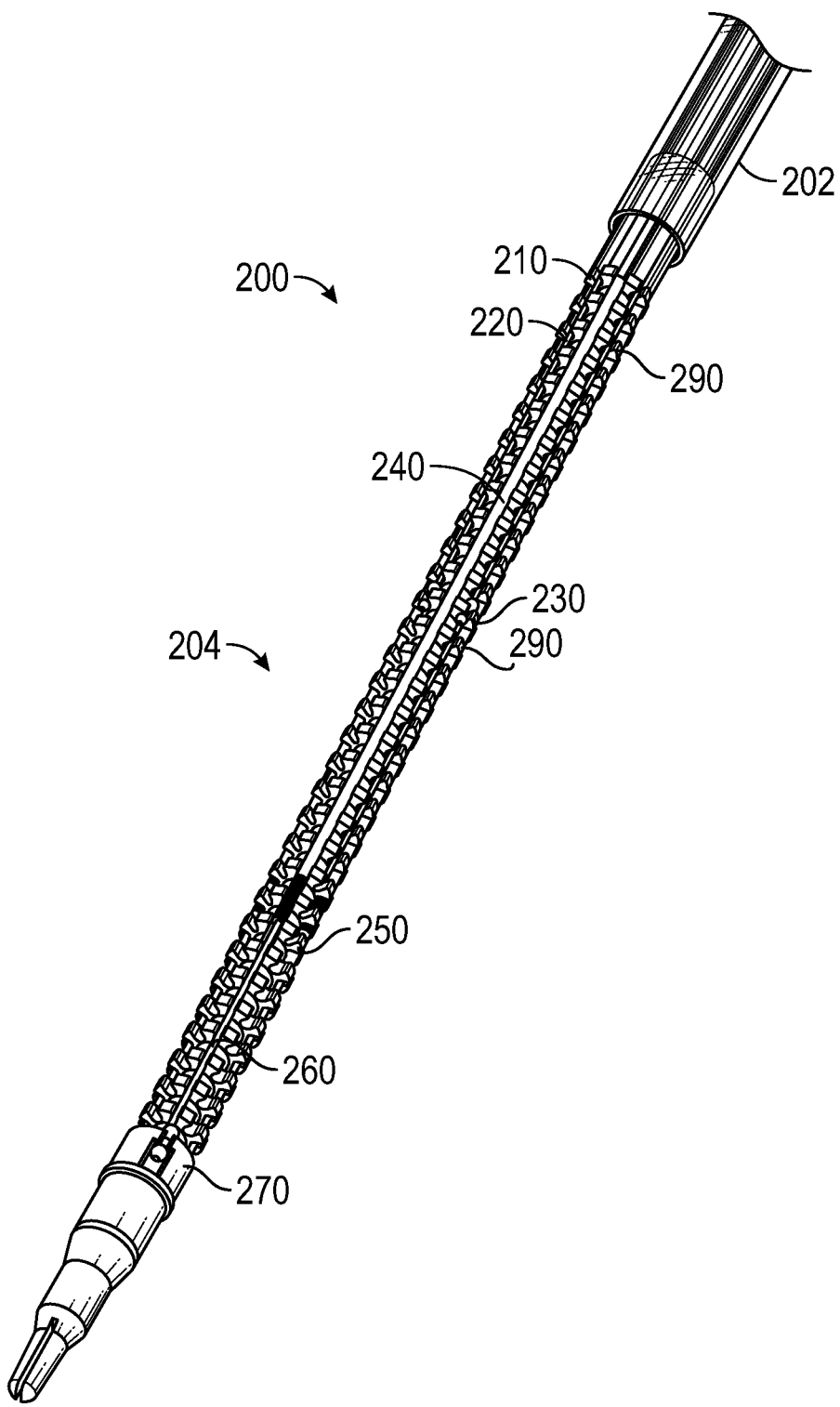

One or more of the first guide 210, the second guide 230, and the third guide 250 can include a plurality of passages, lumens, or channels for inserting, guiding, receiving, and/or engaging one or more control links. As described herein, the plurality of channels can be formed within the guide to permit insertion of a lumen, cable, coil, elongate shaft, tube, or control links. As is illustrated in FIG. 5, the insertion device 200 can include a first plurality of control links 220, a second plurality of control links 240, and a third plurality of control links 260. One or more of the pluralities of control links 220, 240, 260 can extend through and/or engage with one or more of the guides 210, 230, 250, as described herein. At least one of the plurality of control links 220, 240, 260 can be coaxially aligned with and/or overlap at least a portion of any one of another of the pluralities of control links 220, 240, 260. A proximal end of one or more of the plurality of control links 220, 240, 260 can extend beyond the first guide 210 to be actuated by the drive unit 106 to adjust spatial position of one or more of the first guide 210, the second guide 230, the third guide 250, and the tool interface 270 to facilitate repositioning of the one or more instruments (e.g., a surgical tool).

Figure 2:
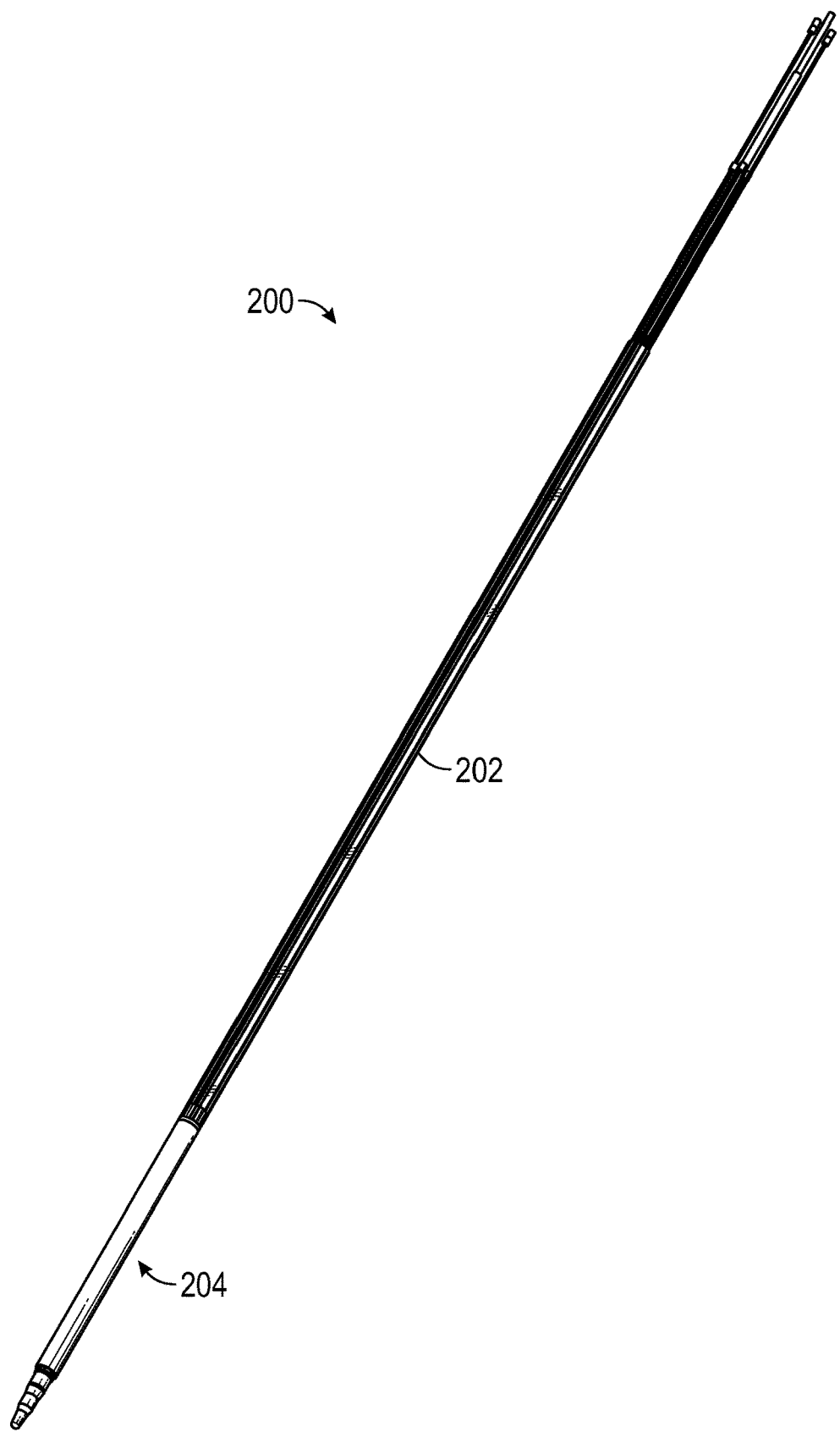
FIGS. 2-9 illustrate an insertion device in accordance with some embodiments.
Figure 3:
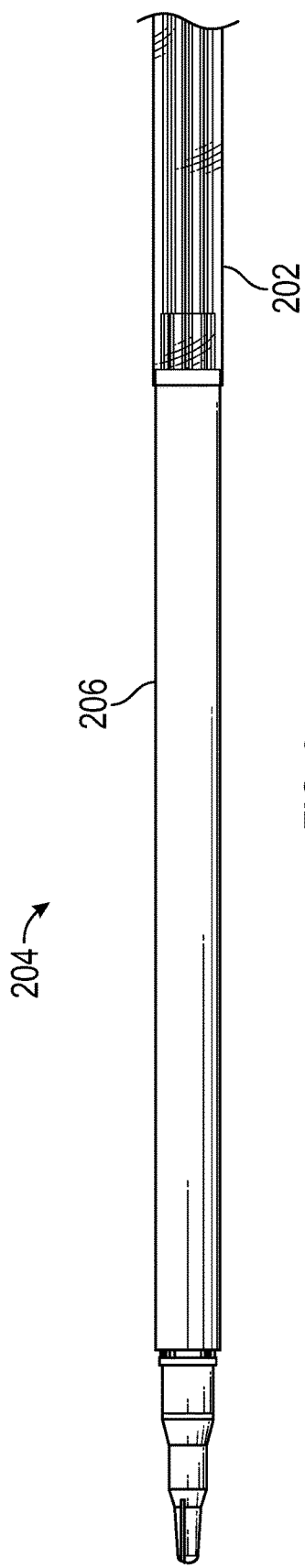
Figure 4:
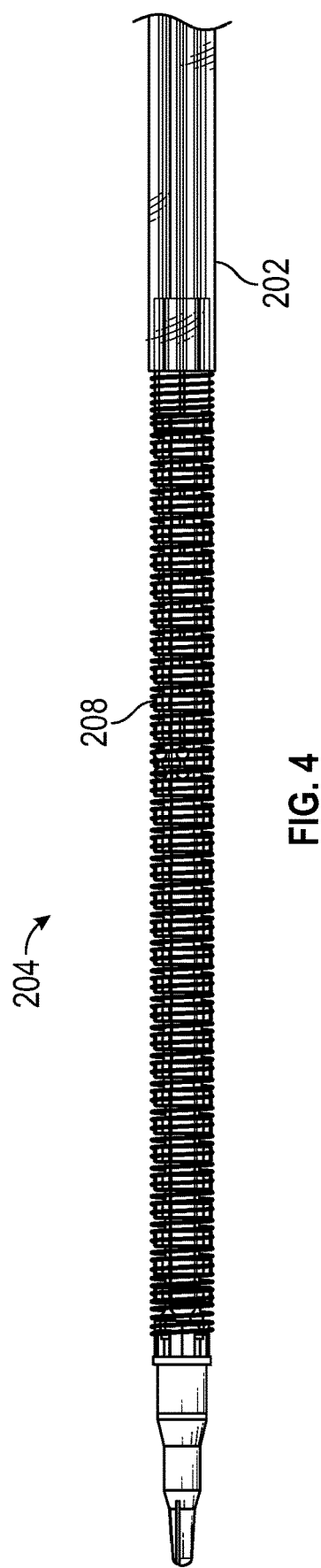

At least a portion of the articulation section 204 can be overlaid and/or enclosed by a support cover. The support cover may inhibit unintentional displacement of one or more components of the articulation section 204 and/or inhibit transfer of fluids into the articulation section 204 from an outside environment. As illustrated in FIGS. 2-4, the support cover can include one or more of an external sheath 206 and a coil 208.

Guides

FIG. 5 illustrates a front perspective view of an insertion device 200, according to some embodiments. As described herein, the articulation section 204 of the insertion device 200 can include a first guide 210, a second guide 230, a third guide 250, and the tool interface 270. One or more of the guides 210, 230, 250 and the tool interface 270 can be configured (for example, sized and/or shaped) to permit one or more of the pluralities of control links 220, 240, 260 to pass through and/or engage the guides 210, 230, 250 and/or the tool interface 270.

The insertion device 200 can include at least one intermediate guide 290, disposed between any one of the first guide 210, the second guide 230, the third guide 250, and the tool interface 270 and another one of the guides 210, 230, 250 or the tool interface 270. For example, with reference to FIG. 5, the insertion device 200 can include a plurality of intermediate guides 290 disposed between the first guide 210 and the second guide 230. However, it will be understood by one having skill in the art that any number of intermediate guides 290 may positioned between any of the guides 210, 230, 250 or the tool interface 270. In some cases, the insertion device 200 comprises at least one of a first intermediate guide 290 coupled to the first guide 210, a second intermediate guide 290 coupled to the second guide 230, a third intermediate guide 290 coupled to the third guide 250, and a fourth intermediate guide 290 coupled to the tool interface 270. Each of the intermediate guides 290 can be coupled to an adjacent intermediate guide 290, the first guide 210, the second guide 230, the third guide 250, or the tool interface 270.

The intermediate guide(s) 290 can include the same or similar structure as the first guide 210, second guide 230, and/or third guide 250 such that the insertion device 200 comprises a plurality of generally coaxially aligned components all having outer surfaces of the same common diameter. As described herein, at least some of the guides 210, 230, 250, 290 can include one or more channels 236 that align with corresponding one or more channels 236 in an adjacent guide 210, 230, 250, 290 such that one or more control links are permitted to pass through at least some of the guides 210, 230, 250, 290.

The guides 210, 230, 250, 290 can be coupled to another guide in a manner that permits bending of the articulation section 204 of the insertion device 200. The articulation section 204 can bend (as described herein) as a result of at least one of pulling or pushing one or more control links positioned along the articulation section 204 that control, for example, the bend, curvature, or another aspect of spatial orientation of one or more of the first guide 210, the second guide 230, the third guide 250, and/or the tool interface 270.

As illustrated in FIGS. 6-9 that shows the first guide 210, the second guide 230, the third guide 250, and the tool interface 270, respectively, the guides 210, 230, 250 and the tool interface 270 can include one or more channels 236 each configured to receive and/or engage one or more of the plurality of control links 220, 240, 260. Unless otherwise noted, the first guide 210, the second guide, the third guide 230 and/or an intermediate guide 290 can include components that are the same as or generally similar to the components discussed herein with reference to the other guides 210, 230, 250, 290. For example, it will be understood that the features described with reference to the second guide 230 shown as in FIGS. 10-12 can be generally the same or similar to any of the other structures described and/or contemplated herein with reference to the first guide 210, the third guide 230, and/or an intermediate guide 290.

Figure 10:
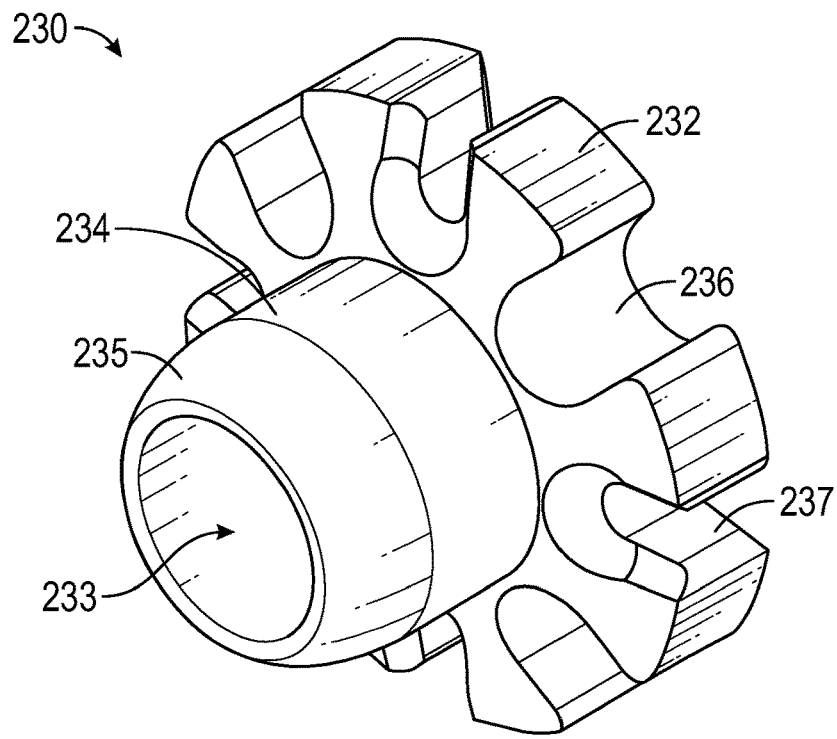
FIGS. 10-12 illustrates a guide in accordance with some embodiments.
Figure 11:
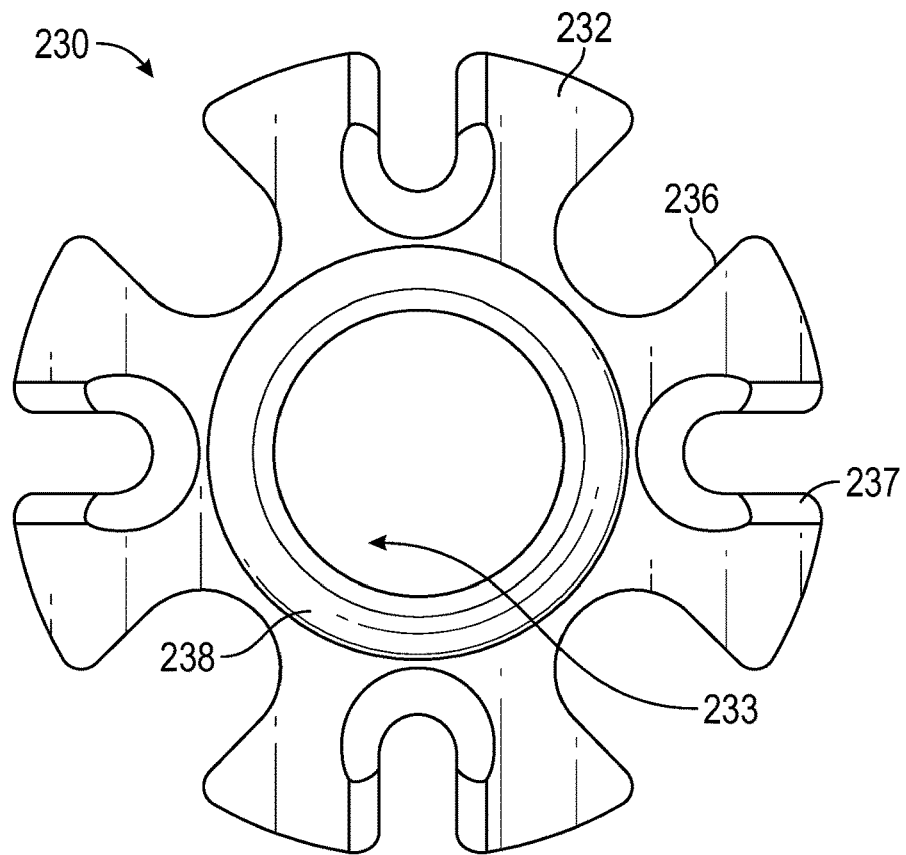
Figure 12:
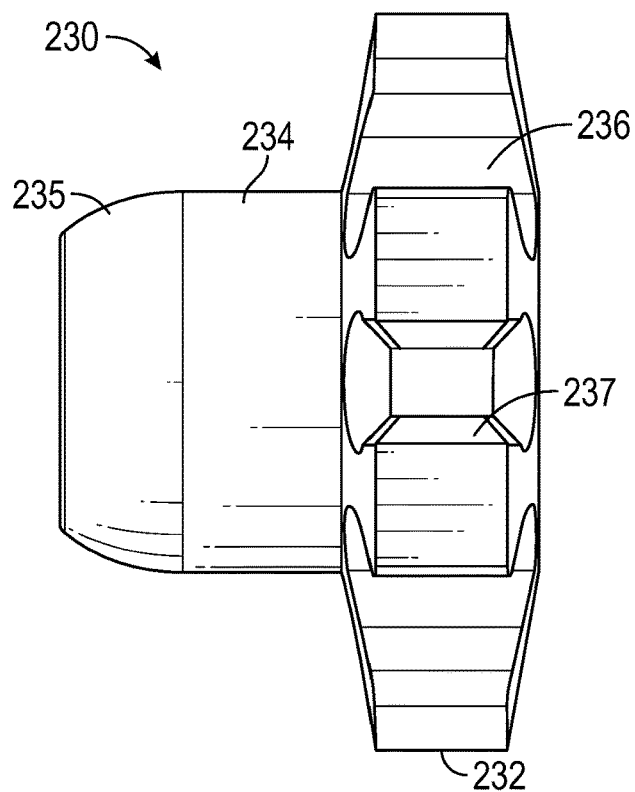

FIGS. 10-12 illustrate that, in certain cases, the guide (e.g., the second guide 230) can have a generally cylindrical base 232 and an axially extending projection 234. The projection 234 of the second guide 230 can have a cross-sectional diameter smaller than a cross-sectional diameter of the base 232 such that the projection 234 extends from the base 232. The smaller cross-sectional diameter of the projection 234 can be configured to interface with the base 232 of an adjacent guide, as described herein. For example, the projection 234 can include a truncated spherical portion 235 through which a central opening 233 is formed. The central opening 233 extends axially through the projection 234 and the base 232.

Figure 13:
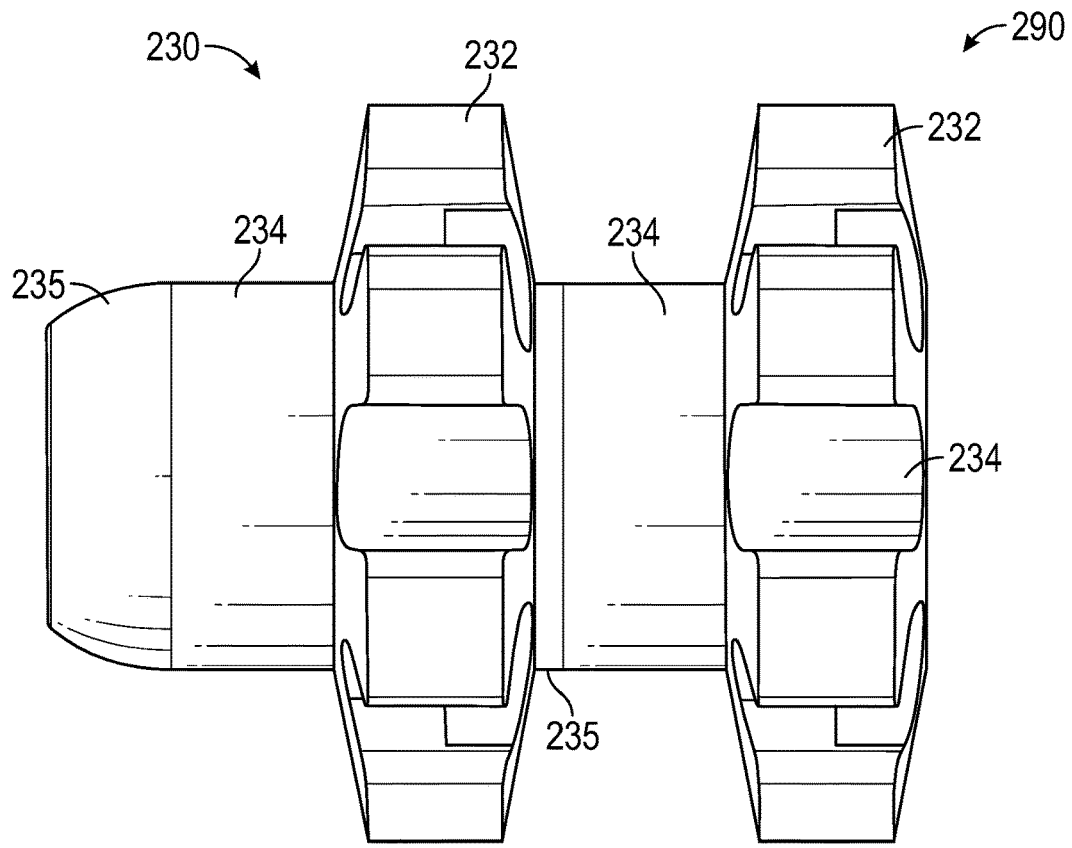
FIG. 13 illustrates coupled guides in accordance with some embodiments.
Figure 14:
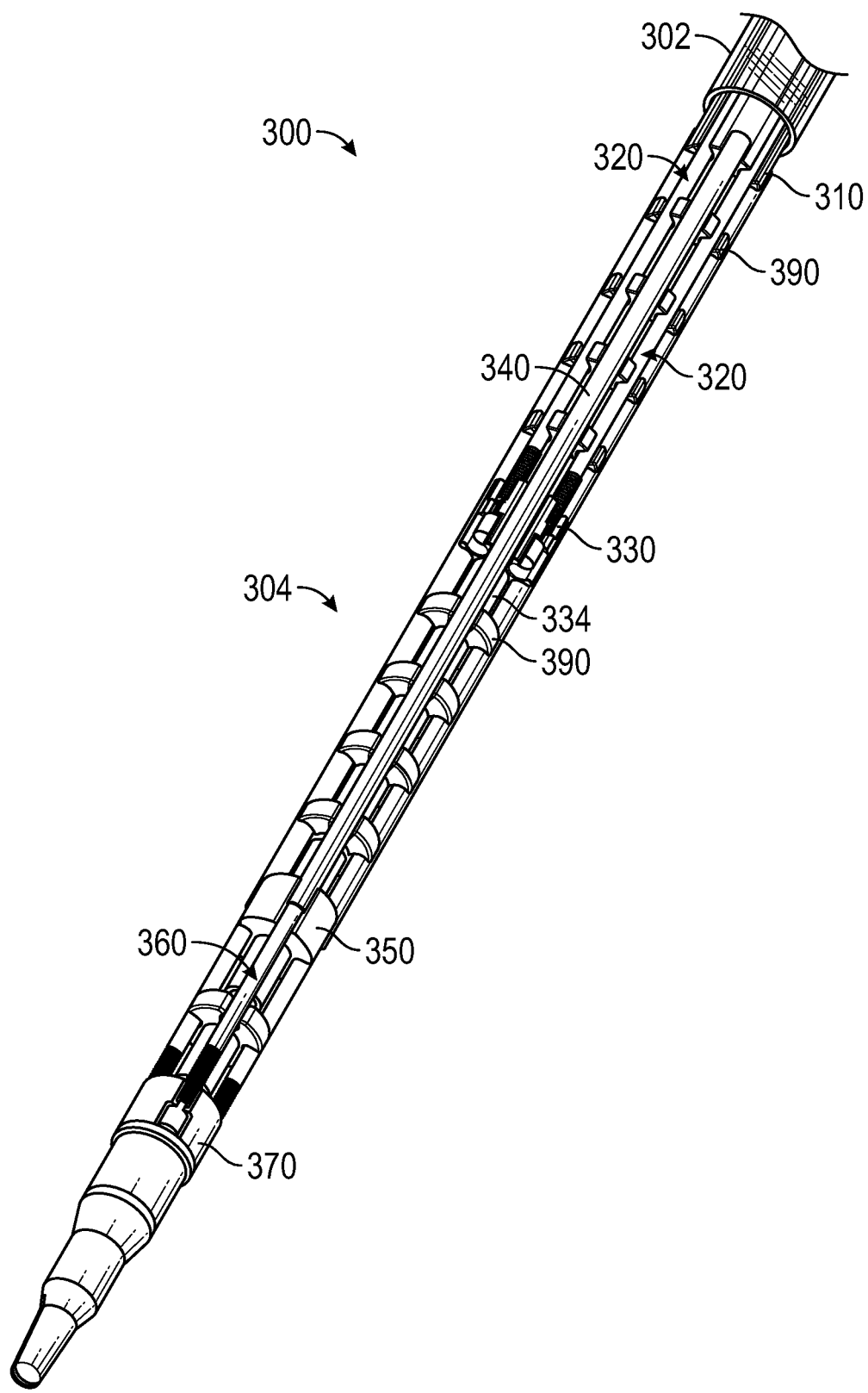
FIGS. 14-16 illustrate an insertion device in accordance with some embodiments.

In some instances, as illustrated in FIG. 11, a proximally-facing end surface of the base 232 includes a socket 238 configured to receive a corresponding projection 234 on an adjacent guide (e.g., an intermediate guide 290). Referring to FIG. 13, the truncated spherical portion 235 and the socket 238 serve to couple a guide (e.g., the second guide 230) with another guide (e.g., the intermediate guide 290). For example, the socket 238 can have a shape complementary to the truncated spherical portion 235 on the projection 234 of an intermediate guide 290 to receive that projection 234 therein. The projection 234 and the socket 238 on the intermediate guide 290 allow the intermediate guide 290 to pivot about the projection 234.

The projection 234 can be integral with the base 232, as illustrated in FIGS. 10-12. However, in some cases, the projection can comprise a component formed separately from the base 232. FIGS. 14-20 show that, in certain cases, an insertion device 300 may comprise a spacer 334 positioned between respective guides (e.g., a second guide 330 and an intermediate guide 390). The spacer 334 can be configured to facilitate engagement and/or movement of a guide relative to an adjacent guide. FIGS. 14-20 are various views of an insertion device 300. It should be understood that, unless otherwise stated, similar reference numerals in FIGS. 14-20 refer to components that are the same as or generally similar to the components in other figures discussed herein with similar features. It will be understood that the features described with reference to insertion device 300 shown in FIGS. 14-20 can be used with any of the embodiments described and/or contemplated herein. It will also be understood that any feature, structure, material, step, or component of any embodiment described and/or illustrated herein (e.g., the insertion device 200) can be used with or instead of any other feature, structure, material, step, or component of any embodiment of the insertion device 300 shown in FIGS. 14-20.

Figure 17:
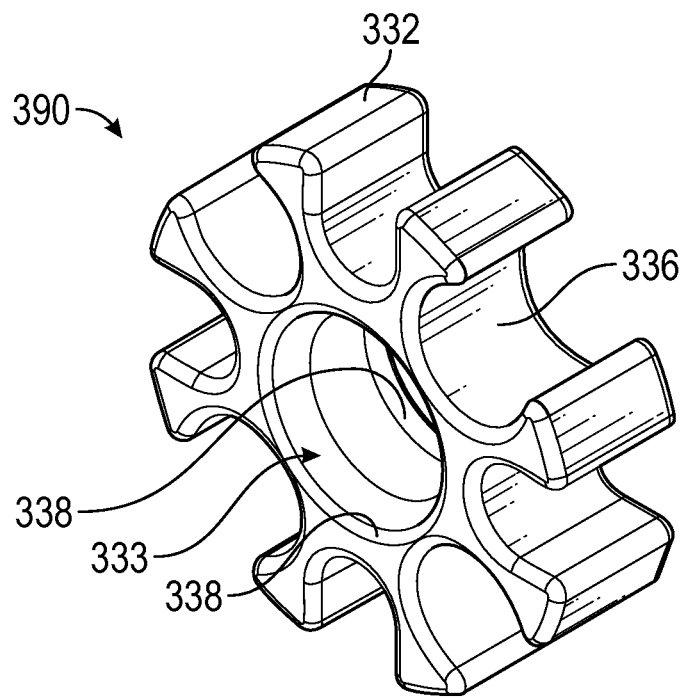
FIGS. 17-18 illustrate guides in accordance with some embodiments.
Figure 18:
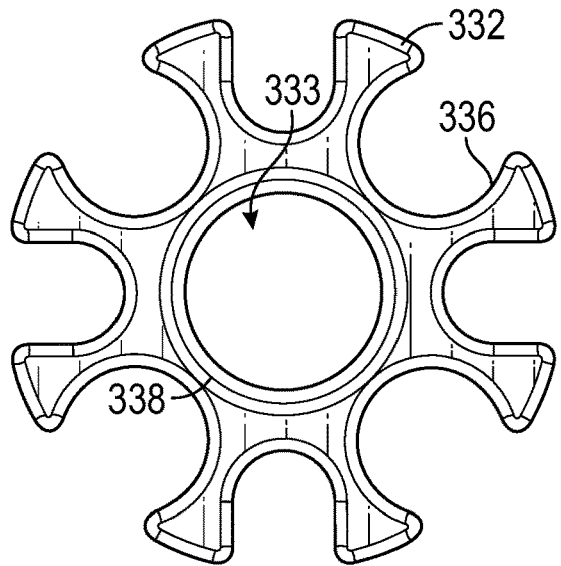
Figure 19:
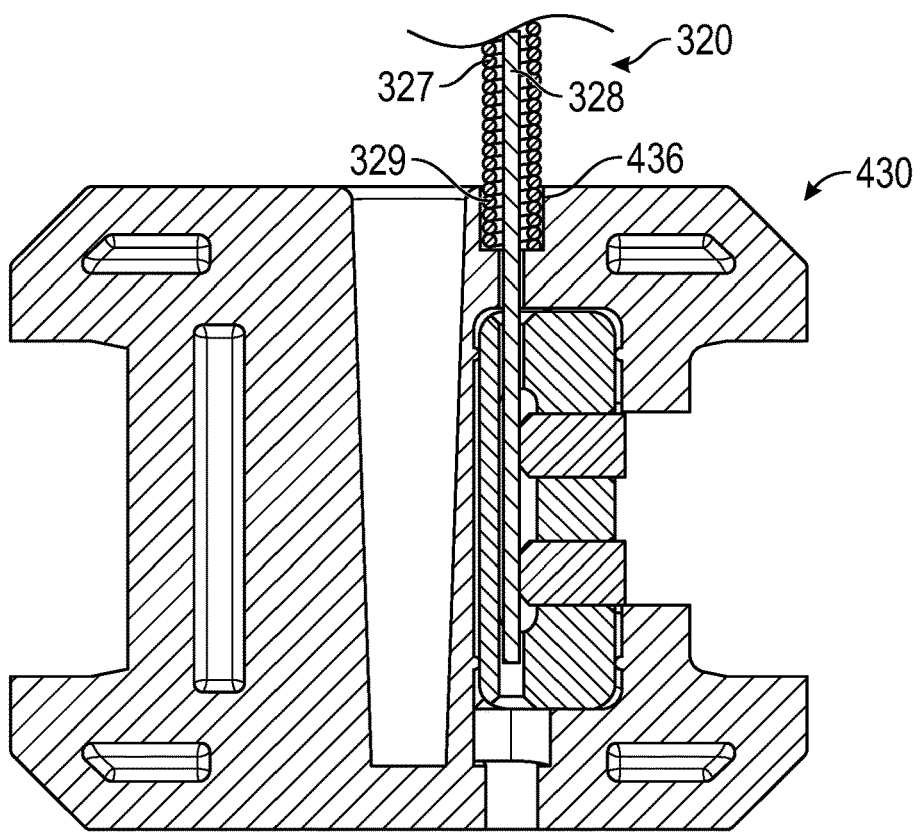
FIG. 19 illustrates an actuator in accordance with some embodiments.

FIGS. 17-18 illustrate that, in certain cases, an intermediate guide 390 can have a generally cylindrical base 332. In some instances, one or both of a proximally-facing end surface and a distally-facing end surface of the base 332 can include a socket 338 configured to receive a corresponding spacer 334 (see FIG. 14) positioned between a first intermediate guide 390 and a second intermediate guide 390. The spacer 334 can include a truncated spherical portion on a proximally-facing surface and/or a distally-facing surface of the spacer 334. The truncated spherical portion and the socket 338 serve to couple the first intermediate guide 390 with another guide. For example, the socket 338 can have a shape complementary to the truncated spherical portion on the spacer 334 to receive that spacer 334 therein. The spacer 334 and the socket 338 on the intermediate guide 290 allow the intermediate guide 290 to pivot about the spacer 334.

With reference again to FIGS. 5-13, the base 232 of the second guide 230 can include a plurality of channels 236 each configured to receive and/or engage with one or more of the plurality of control links 220, 240, 260. The channels 236 may be formed to include an opening having a width sized and shape to correspond with a respective control link such that the respective control link is permitted to pass through and/or engage the base 232.

The plurality of channels 236 can be positioned such one or more of the plurality of control links 220, 240, 260 are in a pre-defined spaced apart relation relative to each other. Generally, the individual control links of each plurality of control links 220, 240, 260 are spaced apart angularly on a circle relative to the other individual control links in the same plurality of control links 220, 240, 260 such that the control links of a given plurality are spaced apart from each other as far as possible. This reduces and balances actuation loads, increases the stiffness of the flexible section and reduces backlash effects as the direction of force on the flexible control links is changed in response to pushing and pulling of the control links.

Figure 6:
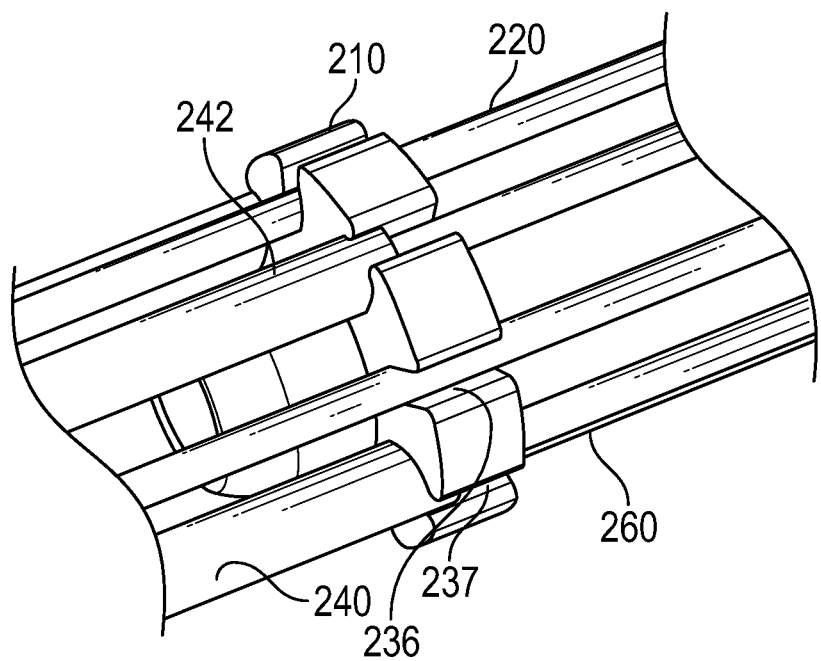

One or more of the channels 236, in some instances, can include an engagement portion (e.g., a ridge 237) configured to reduce a width of the opening and to facilitate engagement of the base 232 with a control link. The ridge 237 can be positioned along a surface of the channel 236. As described in further detail herein, the second guide 230 can include one or more channels 236 configured permit the passage of one or more control links through the second guide 230 and further include one or more additional channels 236 each including an inner ridge 237 configured to engage one or more other control links with the second guide 230. The ridge 237 can permit attachment of the second guide 230 to a control link (e.g., one or more of the first plurality of control links 210). For example, with reference to FIG. 7, the second guide 230 may comprise eight channels including four channels 236 each comprising an inner ridge 237 configured to engage the first plurality of control links 220 and an additional four channels configured to permit the passage of the second plurality of control links 240 and the third plurality of control links 260 through the second guide 230, as described in further detail herein. By way of another example, FIG. 6 illustrates that the first guide 210 may comprise eight channels including four channels 236 each comprising an inner ridge 237 configured to engage the second plurality of control links 240, while permitting passage of the third plurality of control links 260 through the four channels 236, and including an additional four channels configured to permit the passage of the first plurality of control links 220 through the first guide 210, as described in further detail herein. By way of further example, FIG. 8 illustrates that the third guide 250 may comprise four channels 236 each comprising an inner ridge 237 configured to engage the second plurality of control links 240, while permitting passage of the third plurality of control links 260 through the four channels 236, as described in further detail herein However, it will be understood by one having skill in the art that, while the illustrated embodiment shows the guides including eight channels, the guide can be modified to include more or less channels depending on the situation. For example, with reference to FIG. 14, the third guide 350 of the insertion device 300 may comprise four channels each configured to engage a respective control link of the second plurality of control links 340 and/or receive a respective control link of the third plurality of control links 360.

Figure 9:
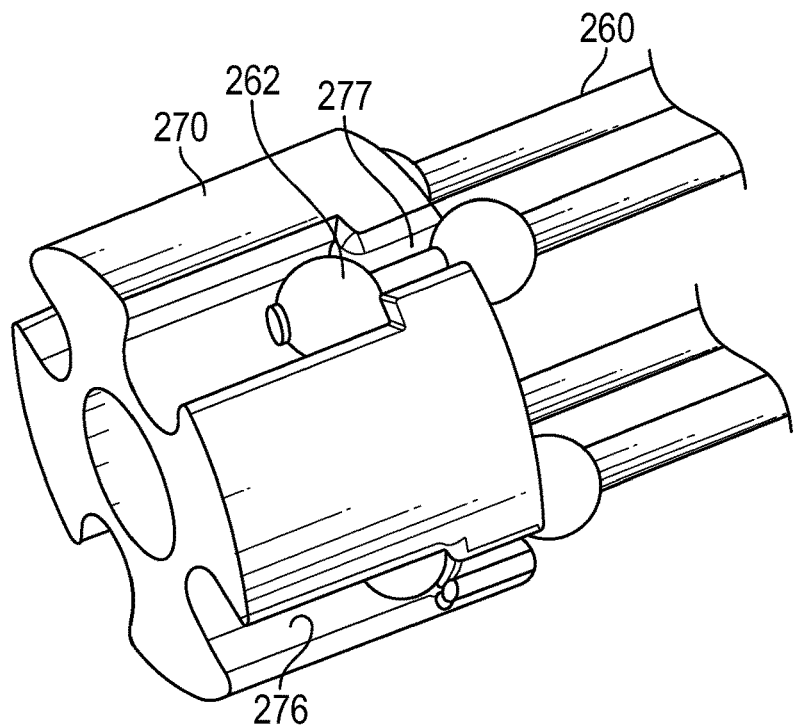

Referring to FIG. 9, the tool interface 270 can include one or more channels 276 configured to receive and/or engage with one or more of the third plurality of control links 260. The channels 276 may be formed to include an opening having a width sized and shape to correspond with a control link of the third plurality of control links 260, such that the respective control link is permitted to pass through and/or engage the tool interface 270. One or more of the channels 276, in some instances, can include an engagement portion (e.g., a ridge 277) configured to reduce a width of the opening and to facilitate engagement of the tool interface 270 with a control link.

The one or more channels 276 of the tool interface 270 can be disposed at locations aligned with one or more channels 236 of an adjacent guide (e.g., the third guide 250 or an intermediate guide 290) to receive and engage a distal end of the third plurality of control links 260.

The tool interface 270 can engage one or more surgical instruments. For example, the one or more instruments can include dexterous tools for performing a surgical procedure. The tool may include one or more of grippers, needle drivers, staplers, dissectors, cutters, hooks, graspers, scissors, coagulators, irrigators, and/or suction devices. Other tool arrangements could alternatively be employed. For example, the tool may alternatively be a cauterizing device, a suction device, an irrigation device, an illumination device, a retraction device or a grasping device.

Referring back to FIG. 5, in the embodiment shown, the insertion device 200 includes several intermediate guides 290 positioned between each of the first guide 210, the second guide 230, the third guide 250, and the tool interface 270 with each of the plurality of control links 220, 240, 260 passing through and/or engaging one or more of the guides 210, 230, 250 and the tool interface 270. The engagement of the one or control links to individual guides can advantageously control tilting or panning of the individual guides and the articulation section 204. The intermediate guides 290 can advantageously enable the articulation section 204 to have pitch and yaw bend components sufficient to define a continuous or substantially continuous arc extending through up to 90 degrees. For example, the pulling and/or pushing of one or more of the first plurality of control links 220 connected to the second guide 230 can control tilting of at least a portion of the articulation section 204. Thus, in some instances, the second guide 230 can be positioned in an orientation in any direction relative to an axis of the first guide 210 up to an angle of about 90 degrees off the axis of the first guide 210. By way of another example, the pulling and/or pushing of one or more of the third plurality of control links 260 connected to the tool interface 270 can control tilting up/down of at least a portion of the articulation section 204 (e.g., a tool engaged with the tool interface 270). In some instances, the tool interface 270 can be positioned in an orientation in any direction relative to an axis of the third guide 250 up to an angle of about 90 degrees off the axis of the third guide 250.

As stated herein, it will be understood that, while the above description references the insertion device 200 of FIGS. 2-13, any feature, structure, material, step, or component of any embodiment described and/or illustrated herein can be used with or instead of any other feature, structure, material, step, or component of any embodiment of the insertion device 300 shown in FIGS. 14-20.

Control Links

As described herein, at least a portion of the articulation section 204 of the insertion device 200 can articulate to permit positioning of a surgical tool at the site of interest. The insertion device 200 can include one or more plurality of control links 220, 240, 260 configured to control movement of various portions of the articulation section 204. In some cases, the first plurality of control links 220 can control pitch/tilt (up/down movement) and/or yaw/pan (left/right movement) of the second guide 230. The third plurality of control links 260 can control pitch/tilt (up/down movement) and/or yaw/pan (left/right movement) of the tool interface 270. The second plurality of control links 240 can control movement of the first guide 210 and the third guide 250 by maintaining the position of the third guide 250 in generally a same or similar orientation as the first guide 210.

The second plurality of control links 240 can maintain the third guide 250 in generally a same or similar orientation as the first guide 210 even as the first plurality of control links 220 and/or the third plurality of control links 260 are being actuated. In some instances, one or more of the second plurality of control links 240, being connected between the first guide 210 and the third guide 250, can be configured to keep the third guide 250 at the same orientation as the first guide 210 when the first plurality of control links 220 move the second guide 230 and/or when the third plurality of control links 260 moves the tool interface 270.

With reference to FIG. 6, one or more of the first plurality of control links 220 can extend through a respective channel 236 of the first guide 210. In the illustrated embodiment, the insertion device 200 includes four first control links 220 each passing through a respective channel 236. Each of the respective channels 236 receiving a control link of the first plurality of control links 220 can be positioned 90° along an outer perimeter of the base 232 of the first guide 210 relative to another channel 236. However, it will be understood that the amount of control links 220 and/or the respective channels 236 may be increased or decreased. Additionally, it will also be understood that the placement of the channels 236 may be altered. For example, the first guide 210 may include four channels 236 positioned by 120°, 60°, 120°, and 60° relative to each other, respectively. By way of another example, the insertion device may include three first control links, such that the first guide 210 comprises three channels positioned 120° relative to the other channels.

One or more of the third plurality of control links 260 can extend through a respective channel 236 of the first guide 210. In some instances, the channel 236 receiving a control link of the third plurality of control links 260 can be different than a channel 236 receiving a control link of the first plurality of control links 220. In the illustrated embodiment, the insertion device 200 includes four third control links 260 each passing through a respective channel 236. Each of the respective channels 236 receiving a control link of the third plurality of control links 260 can be positioned 90° along an outer perimeter of the base 232 of the first guide 210 relative to another channel 236. However, it will be understood that the amount of control links 260 and/or the respective channels 236 may be increased or decreased. Additionally, it will also be understood that the placement of the channels 236 may be altered. For example, the first guide may include four channels positioned by 120°, 60°, 120°, and 60° relative to each other, respectively. By way of another example, the insertion device may include three third control links, such that the first guide comprises three channels positioned 120° relative to the other channels.

One or more of the second plurality of control links 240 can engage with a respective channel 236 of the first guide 210. In some instances, the channel 236 engaging a control link of the second plurality of control links 240 can be different than a channel 236 receiving a control link of the first plurality of control links 220 but be the same as the channel 236 receiving a control link of the third plurality of control links 260. In the illustrated embodiment, the insertion device 200 includes four second control links 240 each engaging a respective channel 236. Each of the respective channels 236 engaging a control link of the second plurality of control links 240 can be positioned 90° along an outer perimeter of the base 232 of the first guide 210 relative to another channel 236. However, it will be understood that the amount of control links 240 and/or the respective channels 236 may be increased or decreased. Additionally, it will also be understood that the placement of the channels 236 may be altered. For example, the first guide may include four channels positioned by 120°, 60°, 120°, and 60° relative to each other, respectively. By way of another example, the insertion device may include three second control links, such that the first guide comprises three channels positioned 120° relative to the other channels.

One or more of the second plurality of control links 240 can engage the first guide 210 and/or the third guide 250 (as described herein with reference to FIG. 8) through various methods. In some instances, with reference to FIG. 6, an end portion 242 of one or more of the second plurality of control links 220 can be configured to engage at least a portion of a respective channel 236 (e.g., the ridge 237 of the respective channel 236) of the first guide 210 to engage the control link 240 with the first guide 210. The control link 240 can be configured to engage the channel 236 by a screw fit, snap fit, interference fit, or otherwise to inhibit disengagement of the control link 240 from an engaged configuration with the first guide 210.

With reference to FIG. 6, as one or more of the third plurality of control links 260 passes through one or more respective channels 236 of the first guide 210 that are engaged with one or more of the second control links 240, one or more of the plurality second control links 240 are configured to at least partially overlap and/or be coaxially aligned with at least a portion of a respective one or more of the plurality of third control links 260. For example, one of the third plurality of control links 260 can be configured to be at least partially nested within one of the second plurality of control links 240, as described in further detail herein.

It will be understood by one having skill in the art that, although the illustrated embodiment shows one of a third control link 260 at least partially positioned within one of a second control link 240, any nesting combination between one or more of any of the plurality of control links 220, 240, 260 may occur. For example, one of the second control links 240 may be positioned within one of the first control links 220 or one of the third control links 260. In some instances, not all links of the third plurality of control links 260 may be nested on or within all the second plurality of control links 240.

The overlapping and/or alignment of individual control links (e.g., a third control link 260 and a second control link 240, as illustrated in FIG. 5) advantageously reduces the amount of links positioned along an outside perimeter of the base of a guide. For example, as illustrated in FIG. 6, nesting of each of the second plurality of control links 240 with each of the third plurality of control links 260 reduces the number of channels and control links positioned along the outer perimeter of the base 232 of the first guide 210 from twelve to eight. This reduction can advantageously decrease any unintentional interaction between the plurality of control links 220, 240, 260 when one or more of the control links 220, 240, 260 are actuated. In some instances, this reduction can increase the flexibility and/or provide better resolution of curvature within the articulated section 204 of the insertion device 200.

Figure 7:
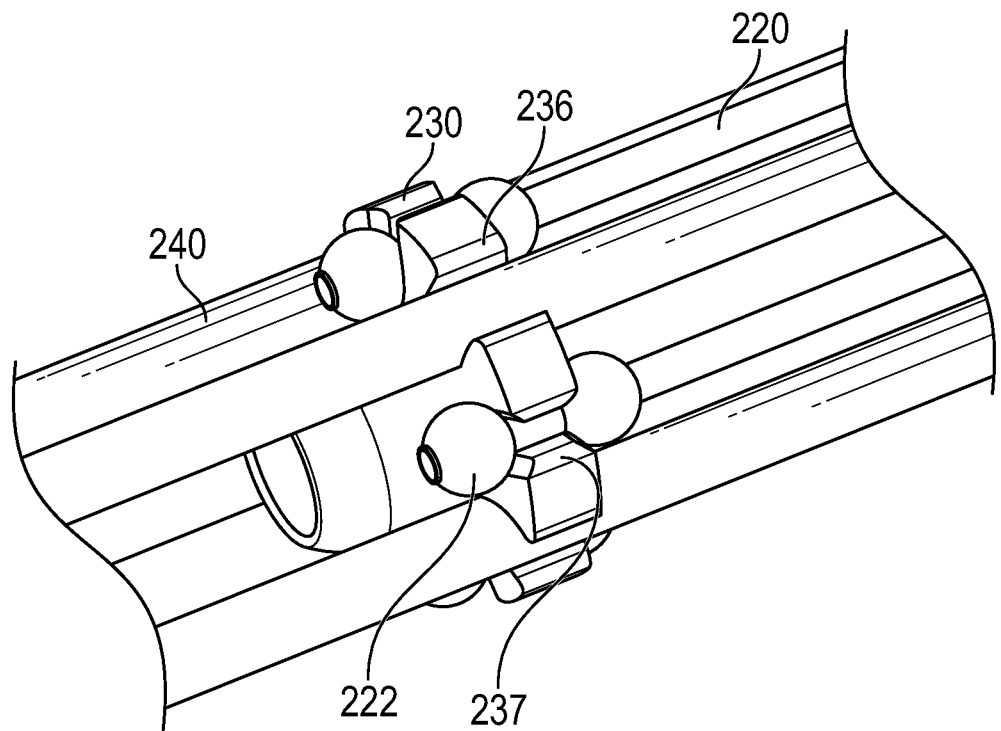
Figure 8:
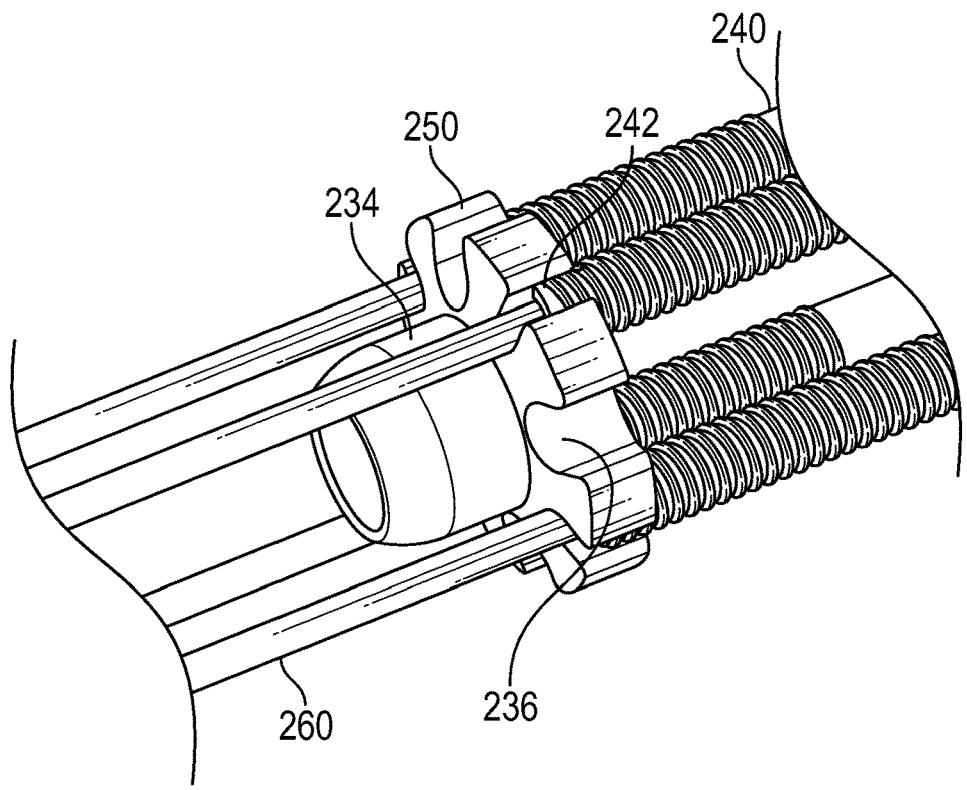

With reference to FIG. 7, one or more of the first plurality of control links 220 can engage a respective channel 236 of the second guide 230. As described above, while the illustrated embodiment shows that the insertion device 200 includes four first control links 220 each engaging a respective channel 236, it will be understood that the amount of control links 220 and/or the respective channels 236 may be increased or decreased and/or that the placement of the channels 236 may be altered.

One or more of the second plurality of control links 240 can extend through a respective channel 236 of the second guide 230. In some instances, the channel 236 engaging a control link of the second plurality of control links 240 can be different than a channel 236 receiving a control link of the first plurality of control links 220 but be the same as the channel 236 receiving a control link of the third plurality of control links 260 when the second plurality of control links 240 are in a nested configuration with the third plurality of control links 260. As described above, while the illustrated embodiment shows that the insertion device 200 includes four second control links 240 each engaging a respective channel 236, it will be understood that the amount of control links 240 and/or the respective channels 236 may be increased or decreased and/or that the placement of the channels 236 may be altered.

With reference to FIG. 8, one or more of the second plurality of control links 240 can engage a respective channel 236 of the third guide 250. As described above, while the illustrated embodiment shows that the insertion device 200 includes four second control links 240 each engaging a respective channel 236, it will be understood that the amount of control links 240 and/or the respective channels 236 may be increased or decreased and/or that the placement of the channels 236 may be altered.

One or more of the third plurality of control links 260 can extend through a respective channel 236 of the third guide 250. In some instances, the channel 236 receiving a control link of the third plurality of control links 260 can be the same as the channel 236 engaging a control link of the second plurality of control links 240 when the second plurality of control links 240 are in a nested configuration with the third plurality of control links 260. As described above, while the illustrated embodiment shows that the insertion device 200 includes four third control links 260 each passing through a respective channel 236, it will be understood that the amount of control links 260 and/or the respective channels 236 may be increased or decreased and/or that the placement of the channels 236 may be altered.

With reference to FIG. 9, one or more of the third plurality of control links 260 can engage a respective channel 276 of the tool interface 270. As described above, while the illustrated embodiment shows that the insertion device 200 includes four third control links 260 each engaging a respective channel 276, it will be understood that the amount of control links 260 and/or the respective channels 276 may be increased or decreased and/or that the placement of the channels 276 may be altered.

One or more of the pluralities of control links 220, 240, 260 can engage, as described herein, at least one of the first guide 210, the second guide 230, the third guide 250, and/or the tool interface 270 through various methods. In some instances, with reference again to FIG. 7, a distal end portion of one or more of the first plurality of control links 220 may include at least one guide connection feature 222. The guide connection feature 222 can protrude from an outer surface of the control link 220. The guide connection feature 222 can be configured to engage the ridge 237 of the respective channel 236 within the second guide 230 to engage the control link 220 with the second guide 230. The guide connection feature 222 can include a peg, a barb, a screw, or other protruding structure, configured to engage the channel 236 by a screw fit, snap fit, interference fit, or otherwise. Each guide connection feature 222 can be configured to inhibit disengagement of the control link 220 from an engaged configuration with the second guide 236. In some embodiments, the guide connection feature 222 is a flange extending radially outward from an end of the control link 220. In some embodiments, the guide connection feature 222 can include an external concave structure that can receive a portion of the ridge 237, as discussed herein. The external concave structure can include a circumferential groove that extends around the control link 222. The circumferential groove can extend entirely around the control link 220, in one embodiment. It will be understood that, while the guide connection feature 222 is discussed with reference to the first plurality of control links 220 and FIG. 7, each of the third plurality of control links 260 can include a guide connection feature 262 configured to engage at least the tool interface 270 in the same or generally similar manner as described herein with reference to the guide connection feature 222.

As stated herein, it will be understood that, while the above description references the insertion device 200 of FIGS. 2-13, any feature, structure, material, step, or component of any embodiment described and/or illustrated herein can be used with or instead of any other feature, structure, material, step, or component of any embodiment of the insertion device 300 shown in FIGS. 14-20.

One or more of the first and/or third pluralities of control links 220, 260 may include a single nitinol wire. In some instances, the nitinol wire can be capable of tension or compression forces without permanent deformation and capable of experiencing up to about 4% strain. Nitinol is an alloy of nickel and titanium having shape memory and super elasticity and its ability to support both tension and compression allows the links to be selectively pushed or pulled with similar forces without permanent deformation, which provides for precise control of the control links, actuation redundancy and increased structural stiffness. Accordingly, each of the first and/or second pluralities of control links 220, 260 are configured to be pushed and/or pulled to move the respective guides the links are engaged with and to achieve a full range of movement of the tool interface 270 relative to the first guide 210.

One or more of the first and/or third pluralities of control links 220, 260 can include a wire, cable, or the like with elasticity that can support at least one of tension or compression without permanent deformation. One or more of the control links 220, 260 can be connected to the one or more guides, as described herein. Movement, such as pulling and/or pushing, of the one or more control links 220, 260 can cause adjustment of the spatial orientation of the one or more guides (e.g., the first guide 210, the second guide 230, and/or the third guide 250) and/or the tool interface 270 and, as a result, one or more portions of the articulation section 204.

In some instances, one or more of the first, second, and/or third pluralities of control links 220, 240, 260 can include a hollow interior configured to receive at least a portion of another control link. With reference to FIG. 5-8, one or more of the second plurality of control links 240 can include a hollow interior configured to receive at least a portion of a respective control link of the third plurality of control links 260. The second control link 240 comprising a hollow interior permits the nesting (e.g., overlapping) configuration, as described herein. The hollow interior, in some embodiments, can be formed by the one or more second plurality of control links 240 being formed as a tube or as a coil. The coil can define a hollow interior configured (e.g., sized and shaped) to receive another control therethrough.

In some instances, the coil can be capable of tension or compression forces without permanent deformation. The coil's ability to support both tension and compression allows the links 240 to be selectively pushed and/or pulled to facilitate maintaining the first guide 210 and the third guide 250 in a generally same or similar orientation. For example, the material properties of a coil of one or more of the second control link 240 can be selected such that actuation of the one or more control links 240 causes at least one of the first guide 210, the second guide 230, the third guide 250, and/or the tool interface 270 to be selectively moved into any of a plurality of orientations defining a substantially continuous curve. As described herein, the coil can be sufficiently tight including a high compression rigidity and a high tension spring force. The coil's ability to support both tension and compression allows the second control link 240 to selectively move at least one of the guides and/or the tool interface and define a substantially continuous curve along at least a portion of the articulation section 204. Accordingly, each of the second plurality of control links 240 are configured to be pushed and/or pulled to move the respective guides the links are engaged with and to achieve a full range of movement of the tool interface 270 relative to the first guide 210. In other instances, where the coil does not have a sufficiently high tension spring force, the coil may only support compression and therefore the respective control link would be selectively pushable to cause movement of the guides to define a substantially continuous curve.

One or more of the first and/or third pluralities of control links 220, 260 can include a wire, cable, or the like with elasticity that can support at least one of tension or compression without permanent deformation. One or more of the control links 220, 260 can be connected to the one or more guides, as described herein. Movement, such as pulling and/or pushing, of the one or more first and/or third pluralities of control links 220, 260 can cause adjustment of the spatial orientation of the one or more guides (e.g., the first guide 210, the second guide 230, and/or the third guide 250) and/or the tool interface 270, and as a result of a coil's elasticity, each of the second plurality of control links 240 can be configured to adjust accordingly.

As described herein, one or more actuators can pull and/or push the one or more control links 220, 260, for example, via rotation in first and/or second directions. Pulling a link 220, 260 can cause shortening its length, while pushing the link can cause lengthening the link (such as, returning the link substantially to its initial length).

As stated herein, it will be understood that, while FIGS. 2-13 illustrate that each of the second plurality of control links 240 is configured to receive a respective control link of a third plurality of control links 260, any one of the first and/or second pluralities of control links 220, 260 can be modified to incorporate any feature, structure, material, step, or component of any embodiment described and/or illustrated herein to be configured to receive any one of the other first, second, and/or third pluralities of control links 220, 240, 260.

Figure 15:
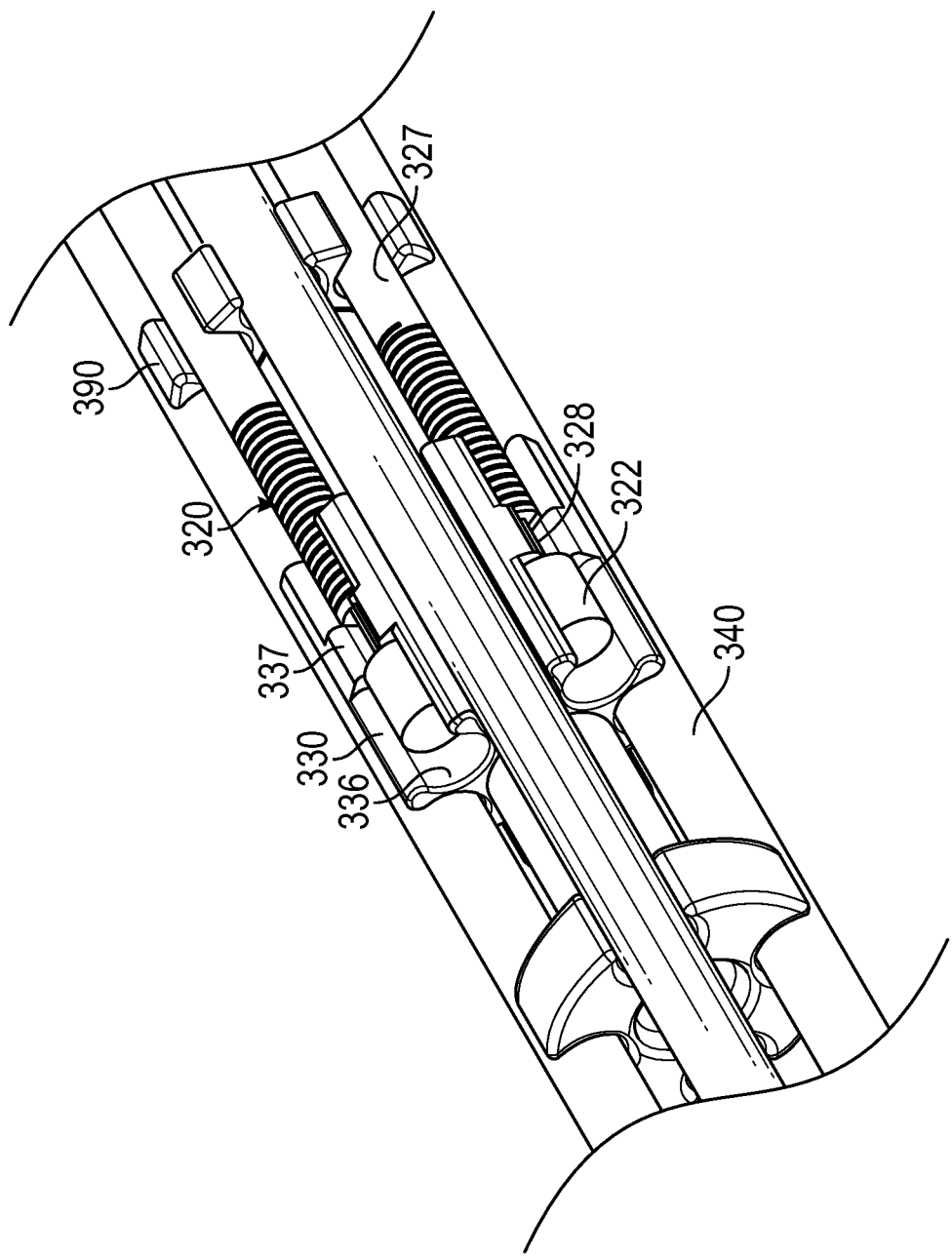

In some embodiments, at least one of the first and/or third pluralities of control links can include an internal control link and an external control link. FIG. 15 shows that, in certain embodiments, at least one of the first plurality of control links 320 may comprise an external control link 327 (e.g., an outer coil) and an internal control link 328 (e.g., inner wire). The external control link 327 can be similar to the coil as described with reference to the second plurality of control links 240 of the insertion device 200. The external control link 327 can include a hollow interior configured to receive at least a portion of the internal control link 328 such that the hollow interior permits the external control link 327 to overlap at least a portion of the internal control link 328. The internal control link 328 can support tension without permanent deformation. One or more of the control links 220, 260 can be connected to the one or more guides, as described herein.

One or more of the external control links 327, in some instances, can include a flexible tube. In some instances, the flexible tube can be capable of tension and/or compression forces without permanent deformation. The flexible tube's ability to support both tension and compression allows the external control links 327 to be selectively pushed and/or pulled to facilitate with similar forces without permanent deformation, which provides for precise control of the control links, actuation redundancy and increased structural stiffness.

The internal control link's 328 ability to support tension, along with the external control link 327 ability to support compression, allows the links 320 to be selectively pulled via the internal control link 328 (e.g., the wire) (such that the external control link 327 becomes compressed) and/or pushed via the external control link 327 (e.g., the flexible tube and/or the coil) (as tension is released on the internal control link 328), which provides for precise control of the control links, actuation redundancy and increased structural stiffness. Movement, such as pulling and/or pushing, of the one or more control links 320 cause adjustment of the spatial orientation of the one or more guides (e.g., the first guide 310, the second guide 330, and/or the third guide 350) and/or the tool interface 370 and, as a result, one or more portions of the articulation section 304.

Figure 16:
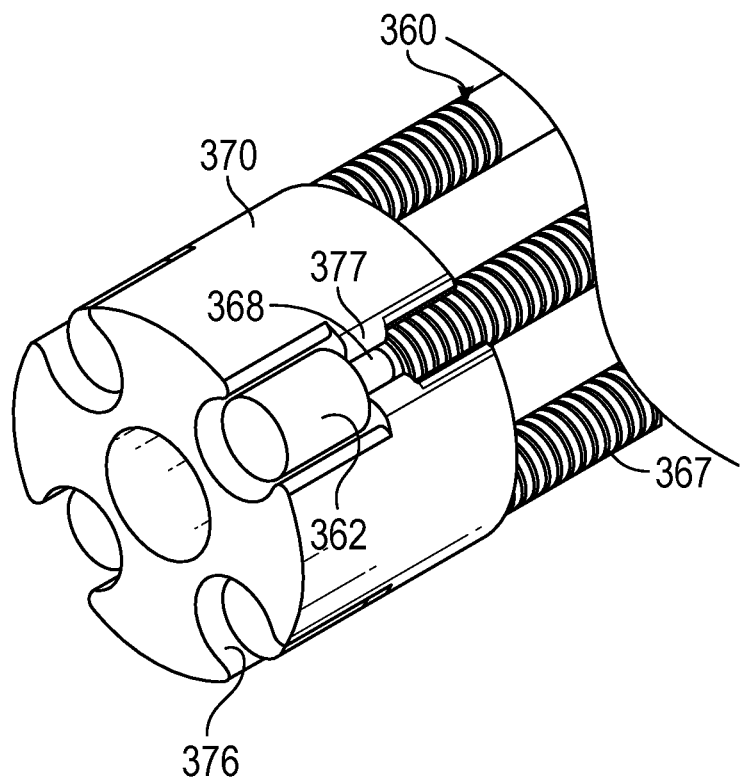

In some instances, the internal control link 328 can include a braided wire, which can simply manufacturability of the internal control link 328 and decrease manufacturing costs with respect to a device including a single nitinol wire. It will be understood that, while the above discussion references the first plurality of control links 320 as shown in FIG. 15, any one of the second and/or third pluralities of control links 340, 360 can be modified to incorporate any feature, structure, material, step, or component of any embodiment described and/or illustrated herein. For example, as illustrated in FIG. 16, the third plurality of control links 360 can include an external control link 367 and an internal control link 368 that are generally the same or similar to the first plurality of control links 320. Accordingly, each of the first and/or second pluralities of control links 320, 360 can be configured to be pushed via the external control link 327, 367 and/or pulled via the internal control link 328, 368 to move the respective guides the links are engaged with and to achieve a full range of movement of the tool interface 370 relative to the first guide 310. For example, pulling the internal control link 328, 368 can cause the tool interface 370 to change position and to compress the external control link 327, 367. As another example, an actuator moving to compress or push the external control link 327, 367 can cause the tool interface 370 to change position and to pull the internal control link 328, 368. Such arrangement can be an alternative to pushing/pulling a nitinol wire.

As described herein, one or more actuators can pull the one or more control links 220, 260, for example, via rotation in first and/or second directions. In some instances where at least one of the first and/or third pluralities of control links 320, 360 comprises an external control link 327, 367 and an internal control link 328, 368, the actuator may be configured to pull on the internal control link 328, 368 causing a compression of the external control link 327, 367. Upon release of the tension caused by the actuator pulling on the internal control link 328, 368, the external control link 327, 367 can apply a restoring force to "push" a corresponding guide to which the external control link 327, 367 is attached, thereby causing the internal control link 328, 368 to be pulled and, thus, extended and returning the internal control link 328, 368 substantially to its initial length. In some instances, such as when the external control link 327, 367 comprises a flexible tube, the actuator may be configured to push on the external control link 327, 367 causing extension of the internal control link 328, 368. The ability to selectively actuate one or more of the external control link 327, 367 and/or the internal control link 328, 368 advantageously allows the user the ability to more directly control individual movement of the various components of the insertion device 200. For example, at least with reference to the third plurality of control links 360, the ability to selectively push the external control link (e.g., coil or flexible tube) and pull the internal control link (e.g., a braided wire) can allow a user to more efficiently and consistently manipulate the tool interface 370 and/or a corresponding surgical tool during use.

One or more of the external control links 327, 367 and/or the internal control link 328, 368 (e.g., a coil and a cable) can be configured to comprise a sufficient tension between the respective links such that the links contain a sufficient amount of rigidity to prevent at least a portion of the articulation section 204 from drooping or sagging as the insertion device 200 is in use. Rigidity can help to reduce the size and/or number of guides while still inhibiting drooping or sagging as the insertion device 200. For example, one or more of the intermediate guides may not be included if a sufficient amount of tension exists between one or more of the external control links 327, 367 and/or the internal control link 328, 368 (e.g., a coil and a cable). A reduction in the size and/or number of guides may improve the degrees of flexibility and movement of the various components of the insertion device 200.

Similar to other embodiments described herein, one or more of the external control link 327, 367 can engage the actuator through various methods. In some instances, with reference to FIG. 19, an end portion 329 of one or more of the external control link 327 of a control link of a first plurality of control links 320 can be configured to engage at least a portion of a respective channel 436 of an actuator assembly 430 to engage the external control link 327 with the actuator assembly 430. The external control link 327 can be configured to engage the channel 436 by a screw fit, snap fit, interference fit, or otherwise to inhibit disengagement of the external control link 327 from an engaged configuration with the actuator assembly 430. The actuator assembly includes an actuator 432. In some cases, the actuator assembly 430 can be similar to the actuator housing 142 and the actuator 432 can be similar to one of the actuators 130 illustrated in FIG. 1B.

Additional details of controlling one or more of the tilt or pan of the insertion device 200 are similar to those described in U.S. Patent Publication No. 2016/0143633 and U.S. Pat. No. 9,629,688, which are assigned to the assignee of the present application and the disclosure of each of which is incorporated by reference in its entirety.

As stated herein, it will be understood that, while the above description references the insertion device 200 of FIGS. 2-13, any feature, structure, material, step, or component of any embodiment described and/or illustrated herein can be used with or instead of any other feature, structure, material, step, or component of any embodiment of the insertion device 300 shown in FIGS. 14-20.

Support Cover

The insertion device 200, in some embodiments as illustrated FIGS. 2-4, can include one or more support covers. At least a portion of the articulation section 204 can be overlaid and/or enclosed by a support cover. The support cover can include one or more of an external sheath 206 and a coil 208. In some instances, the insertion device 200 can include a support cover comprising both an external sheath 206 and a coil 208. The external sheath 206 may be placed in an overlapping position with the coil 208 along at least a portion of the articulation section 204.

The one or more support covers 206, 208 can be flexible or substantially flexible such as to not inhibit movement of one or more portions of the articulation section 204. One or more of support covers 206, 208, in some instances, can contain a sufficient amount of rigidity to prevent at least the tool interface 270 from drooping or sagging as the insertion device 200 is in use. Drooping or sagging can undesirably lead to at least a decrease in the accuracy when navigating the tool interface 270 within a part of the site of interest or inadvertent contact with tissue near or outside the site of interest. Rigidity can help maintain orientation of at least the third guide 250 in same orientation of the first guide 210. In some instances, the one or more support covers can be configured to inhibit displacement of at least one of the first, second, and third pluralities of control links from a respective channel(s) of the first guide, the second guide, the third guide, and/or the tool interface. The one or more support covers can be configured to maintain at least one of the first, second, and third pluralities of control links such that, in some instances, the size and/or number of guides may be reduced while still inhibiting unintentional displacement of at least one of the first, second, and third pluralities of control links from a respective channel(s). For example, one or more of the intermediate guides may not be included if the insertion device includes one or more support covers. A reduction in the size and/or number of guides may improve the degrees of flexibility and movement of the various components of the insertion device 200.

The one or more support covers can be configured to overlay the articulation section 204 to prevent ingress of fluids and/or solids within the articulation section 204. One or more of the support covers 206, 208, in some instances can comprise a fluid impermeable material configured to inhibit the passage of fluid through the support cover 260, 208. Ingress of fluids and/or within the articulation section 204 may negatively impact the use of the insertion device 200 by altering the degrees of flexibility and movement of the various components of the insertion device 200. For example, in some instances, the external sheath 206 may comprise a plastic or other fluid impermeable material configured to inhibit the passage of fluid while maintaining a degree of flexibility such as to not inhibit movement of the articulation section 204.

It will be understood that, while the one or more support covers 206, 208 are discussed with reference to the insertion device 200 of FIGS. 2-13, the one or more support covers 206, 208 can be included in the same or generally similar manner as described herein with reference to the insertion device 300 of FIGS. 14-20.

Other Variations

Those skilled in the art will appreciate that, in some embodiments, additional components and/or steps can be utilized, and disclosed components and/or steps can be combined or omitted. For example, although some embodiments are described in connection with a robotic surgery system, the disclosure is not so limited. Systems, devices, and methods described herein can be applicable to medical procedures in general, among other uses. As another example, certain components can be illustrated and/or described as being circular or cylindrical. In some implementations, the components can be additionally or alternatively include non-circular portions, such as portions having straight lines. As yet another example, any of the actuators described herein can include one or more motors, such as electrical motors.

The foregoing description details certain embodiments of the systems, devices, and methods disclosed herein. It will be appreciated, however, that no matter how detailed the foregoing appears in text, the systems, devices, and methods can be practiced in many ways. The use of particular terminology when describing certain features or aspects of the disclosure should not be taken to imply that the terminology is being redefined herein to be restricted to including any specific characteristics of the features or aspects of the technology with which that terminology is associated.

It will be appreciated by those skilled in the art that various modifications and changes can be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the figures can be combined, interchanged, or excluded from other embodiments.

With respect to the use of substantially any plural and/or singular terms herein, those having skill in the art can translate from the plural to the singular and/or from the singular to the plural as is appropriate to the context and/or application. The various singular/plural permutations can be expressly set forth herein for sake of clarity.

Directional terms used herein (for example, top, bottom, side, up, down, inward, outward, etc.) are generally used with reference to the orientation or perspective shown in the figures and are not intended to be limiting. For example, positioning "above" described herein can refer to positioning below or on one of sides. Thus, features described as being "above" may be included below, on one of sides, or the like.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (for example, the bare recitation of "two recitations," without other modifiers, typically means at least two recitations, or two or more recitations).

The term "comprising" as used herein is synonymous with "including," "containing," or "characterized by," and is inclusive or open-ended and does not exclude additional, unrecited elements or method steps.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function and/or achieves a desired result. For example, the terms "approximately", "about", "generally," and "substantially" may refer to an amount that is within less than 10% of, within less than 5% of, within less than 1% of, within less than 0.1% of, and/or within less than 0.01% of the stated amount.

It will be further understood by those within the art that any disjunctive word and/or phrase presenting two or more alternative terms, whether in the description, claims, or drawings, can be understood to contemplate the possibilities of including one of the terms, either of the terms, or both terms. For example, the phrase "A or B" will be understood to include the possibilities of "A" or "B" or "A and B." Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

The above description discloses embodiments of systems, apparatuses, devices, methods, and materials of the present disclosure. This disclosure is susceptible to modifications in the components, parts, elements, steps, and materials, as well as alterations in the fabrication methods and equipment. Such modifications will become apparent to those skilled in the art from a consideration of this disclosure or practice of the disclosure. Consequently, it is not intended that the disclosure be limited to the specific embodiments disclosed herein, but that it cover all modifications and alternatives coming within the scope and spirit of the subject matter embodied in the following claims.

What is claimed is:

1. An insertion device for a robotic surgery apparatus, the insertion device comprising:
    a first guide comprising a first plurality of channels arranged in an annular array, wherein each channel of the first plurality of channels is open in a radially outward direction;
    a second guide including a second plurality of channels arranged in an annular array, wherein each channel of the second plurality of channels is open in a radially outward direction;
    a tool interface configured to engage a surgical tool configured to perform robotic surgery; and
    a first plurality of control links each comprising a first distal end portion including a guide connection feature having:
    a first protruding structure located distal of and in contact with the second guide; and
    a second protruding structure located proximal of and in contact with the second guide, wherein the first and second protruding structures directly engage the second guide to transmit at least one of a push or pull force thereto, each of the first plurality of control links extending through a respective channel of the first plurality of channels of the first guide.

2. The insertion device of claim 1, further comprising:
    a third guide including a third plurality of channels arranged in an annular array, wherein each channel of the third plurality of channels is open in a radially outward direction, wherein the first plurality of guide channels, the second plurality of guide channels and the third plurality of guide channels are axially aligned with one another;
    a second plurality of control links each including:
        a first end portion that engages the first guide, and
        a second end portion that engages the third guide,
    wherein each of the second plurality of control links extends through a respective channel of the second plurality of channels of the second guide; and
    a third plurality of control links each comprising a first distal end portion including a guide connection feature having:
        a first protruding structure located distal of and in contact with the tool interface; and
        a second protruding structure located proximal of and in contact with the tool interface, wherein the first and second protruding structures of the third plurality of control links directly engage the tool interface to transmit the at least one push or pull force thereto, each of the third plurality of control links extending through respective channels of the third plurality of channels of the third guide and further extending through the respective channels of the second plurality of channels of the second guide, each of the third plurality of control links including a portion that passes through a respective second control link of the second plurality of control links.

3. The insertion device of claim 2, wherein each of the first plurality of channels of the first guide are sized to receive a respective control link of any one of the first plurality of control links, the second plurality of control links, or the third plurality of control links.

4. The insertion device of claim 2, wherein each of the second plurality of channels of the second guide are sized to receive a respective control link of any one of the first plurality of control links or the second plurality of control links.

5. The insertion device of claim 2, wherein each of the third plurality of channels of the third guide are sized to receive a respective control link of any one of the second plurality of control links and the third plurality of control links.

6. The insertion device of claim 2, wherein each of the second plurality of control links comprises a hollow interior portion through which the portion of a respective third control link passes.

7. The insertion device of claim 2, wherein each of the first plurality of control links comprises an external control link defining an internal pathway and an internal control link, and wherein at least a portion of each of the internal control links pass through a respective internal pathway.

8. The insertion device of claim 2, wherein each of the third plurality of control links comprises an external control link defining an internal pathway and an internal control link, and wherein at least a portion of each of the internal control links pass through a respective internal pathway.

9. The insertion device of claim 2, further comprising at least one first intermediate guide positioned between the first guide and the second guide.

10. The insertion device of claim 9, wherein the at least one first intermediate guide comprises a respective first guide and a respective second guide, wherein the first guide of the at least one first intermediate guide engages the first guide, and wherein the second guide of the at least one first intermediate guide engages the second guide.

11. The insertion device of claim 2, further comprising at least one second intermediate guide positioned between the second guide and the third guide.

12. The insertion device of claim 11, wherein the at least one second intermediate guide comprises a first guide and a second guide, wherein the first guide of the at least one second intermediate guide engages the second guide, and wherein the second guide of the at least one second intermediate guide engages the third guide.

13. An insertion device for a robotic surgery apparatus, the insertion device comprising:
a first guide comprising a first plurality of channels;
a second guide including a second plurality of channels;
an instrument interface configured to engage a surgical instrument; and
a first plurality of control links comprising a plurality of distal first ends including a plurality of respective guide connection features having a first protruding structure located distal of the second guide and a second protruding structure located proximal of the second guide, wherein the second guide is disposed immediately between the first and second protruding structures of the first plurality of control links to transmit at least one of a push or pull force thereto, each of the first plurality of control links passing through a respective channel of the first plurality of channels of the first guide.

14. The insertion device of claim 13, further comprising:
a third guide including a third plurality of channels;
a second plurality of control links comprising a plurality of first ends that engage the first guide and a plurality of second ends that engage the third guide, wherein each of the second plurality of control links passes through a respective channel of the second plurality of channels of the second guide; and
a third plurality of control links comprising a plurality of distal first ends including a plurality of respective guide connection features having a first protruding structure located distal of the instrument interface and a second protruding structure located proximal of the instrument interface, wherein the instrument interface is disposed immediately between the first and second protruding structures of the third plurality of control links to transmit the at least one push or pull force thereto, each of the third plurality of control links passing through a respective channel of the third plurality of channels of the third guide and further passing through the respective channel of the second plurality of channels of the second guide, at least one control link of the third plurality of control links being coaxially aligned with a respective second control link of the second plurality of control links.

15. The insertion device of claim 14, wherein each of the first plurality of channels are sized to receive a respective control link of any one of the first plurality of control links, the second plurality of control links, or the third plurality of control links.

16. The insertion device of claim 14, wherein each of the second plurality of channels are sized to receive a respective control link of any one of the first plurality of control links or the second plurality of control links.

17. The insertion device of claim 14, wherein each of the third plurality of channels are sized to receive a respective control link of any one of the second plurality of control links and the third plurality of control links.

18. The insertion device of claim 14, wherein the respective second control link of the second plurality of control links comprises a hollow interior portion through which a portion of the at least one control link of the third plurality of control links passes.

19. The insertion device of claim 14, wherein each of the first plurality of control links comprises an external control link defining an internal pathway and an internal control link, and wherein at least a portion of each of the internal control links pass through a respective internal pathway.

20. The insertion device of claim 14, wherein each of the third plurality of control links comprises an external control link defining an internal pathway and an internal control link, and wherein at least a portion of each of the internal control links pass through a respective internal pathway.

21. The insertion device of claim 14, further comprising:
at least one first intermediate guide positioned between the first guide and the second guide;
at least one second intermediate guide positioned between the second guide and the third guide; and
at least one third intermediate guide positioned between the third guide and the instrument interface.

* * * * *